US012747261B2

(12) United States Patent
Warminski et al.

(10) Patent No.: US 12,747,261 B2
(45) **Date of Patent: *Sep. 29, 2026**

(54) MRNA 5'-END CAP ANALOGS MODIFIED WITHIN PHOSPHATE RESIDUES, RNA MOLECULE INCORPORATING THE SAME, USES THEREOF AND METHOD OF SYNTHESIZING RNA MOLECULE OR PEPTIDE

(71) Applicants: Uniwersytet Warszawski, Warsaw (PL); Explorna Therapeutics Sp. z o.o., Warsaw (PL)

(72) Inventors: Marcin Warminski, Warsaw (PL); Pawel Sikorski, Warsaw (PL); Joanna Kowalska, Warsaw (PL); Jacek Jemielity, Warsaw (PL)

(73) Assignees: Uniwersytet Warszawski, Warsaw (PL); Explorna Therapeutics Sp. z o.o., Warsaw (PL)

( * ) Notice: Subject to any disclaimer, the term of this patent is extended or adjusted under 35 U.S.C. 154(b) by 853 days.

This patent is subject to a terminal disclaimer.

(21) Appl. No.: 17/798,102

(22) PCT Filed: Feb. 12, 2021

(86) PCT No.: PCT/PL2021/050006
§ 371 (c)(1),
(2) Date: Aug. 8, 2022

(87) PCT Pub. No.: WO2021/162566
PCT Pub. Date: Aug. 19, 2021

(65) Prior Publication Data

US 2023/0295215 A1 Sep. 21, 2023

(30) Foreign Application Priority Data

Feb. 12, 2020 (PL) ........................................ 432884

(51) Int. Cl.
*C07H 21/02* (2006.01)
*C12N 15/11* (2006.01)
*C12P 21/02* (2006.01)

(52) U.S. Cl.
CPC ............ *C07H 21/02* (2013.01); *C12N 15/11* (2013.01); *C12P 21/02* (2013.01); *C12N 2310/317* (2013.01); *C12N 2310/336* (2013.01)

(58) Field of Classification Search
CPC ..................................................... C07H 21/02
See application file for complete search history.

(56) References Cited

FOREIGN PATENT DOCUMENTS

| | | | | | |
|---|---|---|---|---|---|
| WO | WO2017053297 | A1 | | 3/2017 | |
| WO | WO2017066797 | A1 | | 4/2017 | |
| WO | WO-2017130151 | A1 | * | 8/2017 | ............. A61P 35/00 |
| WO | WO2019175356 | A1 | | 9/2019 | |
| WO | WO2021/162567 | A1 | | 8/2021 | |
| WO | 2022051677 | A1 | | 3/2022 | |

OTHER PUBLICATIONS

Grudzien et al: "Differential inhibition of mRNA degradation pathways by novel cap analogs", Journal of Biological Chemistry, vo1. 281 (4), (2006), pp. 1857-1867.
Jemielity et al: •"Synthetic mRNA cap analogs with a modified triphosphate bridge synthesis, applications and prospects", New Journal of Chemistry, vol. 34 (5), (2010), p. 829.
Sikorski et al: "The identity and methylation status of the first transcribed nucleotide in eukaryotic mRNA 5' cap modulates protein expression in living cells", Nucleic Acids Research, vol. 48 (4), (2020), pp. 1607-1626.
Ishikawa et al, "Preparation of eukaryotic mRNA having differently methylated adenosine at the 5'-terminus and the effect of the methyl group in translation", Nucleic Acids Symposium Series No. 53, 2009, 129-130.
Rydzik et al, "Synthetic dinucleotide mRNA cap analogs with tetraphosphate 5',5' bridge containing methylenebis (phosphonate) modification", Org. Biomol. Chem, 2009, 7, 4763-4776.
European Patent Office, Communication of Third Party Observation, EP Appln. 21754329.7, Oct. 4, 2024.
European Patent Office, Supplementary European Search Report, EP Appln. 21754329.7, Dec. 1, 2023.
Kowalska Joanna et al: "Synthesis and characterization of mRNA cap analogs containing phosphorothioate substitutions that bind tightly to elF4E and D4 are resistant to the decapping pyrophosphatase DcpS", RNA, vol. 14, No. 6, Jun. 1, 2008 (Jun. 1, 2008), pp. 1119-1131.
Pawel J. Sikorski et al. (2020), "The identity and methylation status of the first transcribed nucleotide in eukaryotic mRNA 5 cap modulates protein expression in living cells", Nucleic Acids Research, 2020, vol. 48, No. 4, pp. 1607-1626, published online on Jan. 27, 2020; doi: 10.1093/nar/gkaa032.
Ishikawa Masahide et al. (2009), "Preparation of eukaryotic mRNA having differently methylated adenosine at the 5'-terminus and the effect of the methyl group in translation", Nucleic Acids Symposium Series, 53(1), pp. 129-130, (Symposium date: Sep. 27, 2009); doi: 10.1093/nass/nrp065.

* cited by examiner

*Primary Examiner* — Bahar Craigo
(74) *Attorney, Agent, or Firm* — Arrigo, Lee, Guttman & Mouta-Bellum LLP

(57) ABSTRACT

The invention relates to new 5'mRNA end cap analogs, RNA molecules containing them, their uses and methods for their in vitro synthesis, as well as a method for protein or peptide synthesis in vitro or in cell cultures, which method translates the RNA molecule.

9 Claims, 6 Drawing Sheets

Specification includes a Sequence Listing.

MRNA 5'-END CAP ANALOGS MODIFIED WITHIN PHOSPHATE RESIDUES, RNA MOLECULE INCORPORATING THE SAME, USES THEREOF AND METHOD OF SYNTHESIZING RNA MOLECULE OR PEPTIDE

TECHNICAL FIELD

This invention relates to novel mRNA 5'-end cap analogs modified within phosphate residues, an RNA molecule incorporating the same, uses thereof and a method of synthesizing the RNA molecule in vitro, as well as a method of synthesizing a protein or peptide in vitro or in cells, said method comprising translating the RNA molecule.

STATE OF THE ART

The 7-methylguanosine ($m^7G$) cap present at the 5' end of eukaryotic mRNAs plays a crucial role in numerous fundamental cellular processes, mainly by protecting mRNA from premature degradation and serving as a molecular platform for proteins participating in mRNA transport and translation.[1] Thus, chemical modifications of the 5' cap pave the way to design of molecular tools for selective modulation of cap-dependent processes and, consequently, mRNA metabolism.[2] The presence of the 5' cap is necessary for mRNA surveillance and efficient translation under normal conditions. Chemically synthesized mRNA cap analogs of $m^7$GpppG type are utilized as reagents for in vitro synthesis of capped mRNAs.[3]

In vitro transcribed (IVT) 5'-capped mRNAs are useful tools for studying mRNA translation, transport, and turnover, and are an emerging class of highly promising therapeutic molecules. IVT mRNAs find application in protein expression in eukaryotic cell extracts, cultured cells, or even whole organisms. Finally, IVT mRNAs have recently gained great attention as a tool for safe exogenous protein delivery for the purpose of anti-cancer and anti-viral vaccinations and gene-replacement therapies.[4]

The synthesis of 5'-capped mRNAs using mRNA cap analogs can be achieved by in vitro transcription.[3] By this method, called co-transcriptional capping, the synthesis of RNA is performed by RNA polymerase on DNA template in the presence of all 4 NTPs and a cap dinucleotide, such as $m^7$GpppG. The DNA template is usually designed to incorporate G as the first transcribed nucleotide. The polymerase initiates the transcription from GTP or $m^7$GpppG, thereby incorporating one of the nucleotides at the 5' end of the nascent RNA. To increase the percentage of cap analogue incorporation (capping efficiency), the GTP concentration is decreased relative to the other NTPs, and the concentration of the cap dinucleotide is elevated (from 4- to 10-fold excess relative to GTP). Unfortunately, reverse incorporation of cap dinucleotides can potentially occur, resulting in a fraction of 'Gpppm$^7$G-capped' RNAs, which are translationally inactive. This problem has been solved by the discovery of 'anti-reverse cap analogs' (ARCAs) that are modified at the 2'- or 3'-positions of 7-methylguanosine (usually by replacing one of OH groups by $OCH_3$) to block reverse incorporation.[5,6]

Modifications that confer to cap analogs ARCA properties lead to mRNAs modified within 7-methylguanosine; the effects of these modifications on various processes involved in mRNA expression and metabolism have not yet been fully investigated. Another limitation to the use of $m^7$GpppN-type dinucleotides (where N=any nucleotide) is the inability to introduce natural epigenetic modifications within N, such as 2'-O-methylation or methylation of adenosine at position N6[19]. Modifications of this type occur naturally in some eukaryotic mRNAs and have important, though not yet fully understood, biological functions, but their introduction within the N in the $m^7$GpppN structure can result in a significant reduction in the efficiency of incorporation into the mRNA (in the case of methylation at the N6 position of adenine) or reverse incorporation of cap into the mRNA (in the case of 2'-O-methylation of N or a combination of both modifications)[20] mRNAs that have been obtained with dinucleotides can be subjected to 2'-O-methylation within the first transcribed nucleotide enzymatically, e.g., using the commercially available enzyme VCE[21]. However, this solution increases the cost of synthesis and represents an additional step in the mRNA preparation process, which is particularly disadvantageous for mRNAs for therapeutic applications. Another known solution to the problem is the use of cap analogs with the general structure $m^7$GpppN*pG, where N* is a natural nucleotide that can be epigenetically modified by methylation[20,22].

It has been shown that co-transcriptional capping method enables incorporation of various modified cap structures at the RNA 5' end. These modified cap structures may carry molecular tags or confer new properties to mRNA such as increased translation efficiency and stability. Especially beneficial dinucleotide cap analogs are among those modified in the triphosphate bridge.[7] It has been shown that even single atom substitutions in the 5',5'-triphosphate bridge can affect the properties of mRNAs significantly. For example, a single atom substitution at the β-position of the oligophosphate bridge of the cap, introduced by the so-called β-S-ARCA, led to significant increase in translation efficiency of mRNA in vitro and in vivo,[8,9] whereas a single O to $CH_2$ substitution at the α-β position led to decrease in translation efficiency.[10] The dramatically different biological effects of different single-atom substitutions within the cap indicate on high sensitivity of the translational machinery to oligophosphate chain modification and suggests this is a field for further exploration. Such modifications of cap structure sometimes might affect the process of mRNA synthesis, decreasing capping efficiency[23] and overall translation efficiency.

The state of the art indicates that subjecting in vitro transcribed mRNA to the procedure of enzymatic removal of uncapped (5' triphosphate) RNA and purification by HPLC reduces the immunogenicity of mRNA and increases the in vivo expression efficiency of proteins encoded by such mRNA[11,12] However, the removal of uncapped mRNA by the enzymatic method is time consuming and expensive, so in some applications it is preferable to obtain mRNA molecules that are efficiently expressed even if they have not been subjected to the procedure of uncapped mRNA removal.

The purpose of the invention is to provide new mRNA 5 end (cap) analogs that will enable obtaining mRNAs with higher capping efficiency and yielding higher expression levels of proteins encoded by these mRNAs compared to mRNAs obtained using prior art cap analogs, particularly in the art, in which the mRNA used has not undergone prior enzymatic treatment to remove uncapped mRNA.

It is a particular purpose of the invention to provide 5' end mRNA analogs which do not require modification of the OH groups belonging to the ribose of 7-methylguanosine moiety for ensuring incorporation of the cap analogue in the correct orientation.

It is also a particular aim of the invention to provide analogs of the 5' end of mRNAs that do not decrease, but preferably increase, the translation efficiency of the mRNAs containing them.

THE DESCRIPTION OF THE INVENTION

The object of the invention is novel trinucleotide analogs of the 5' end of mRNA (cap analogs) modified within phosphate residues as defined below.

An embodiment of the invention is a compound of the formula:

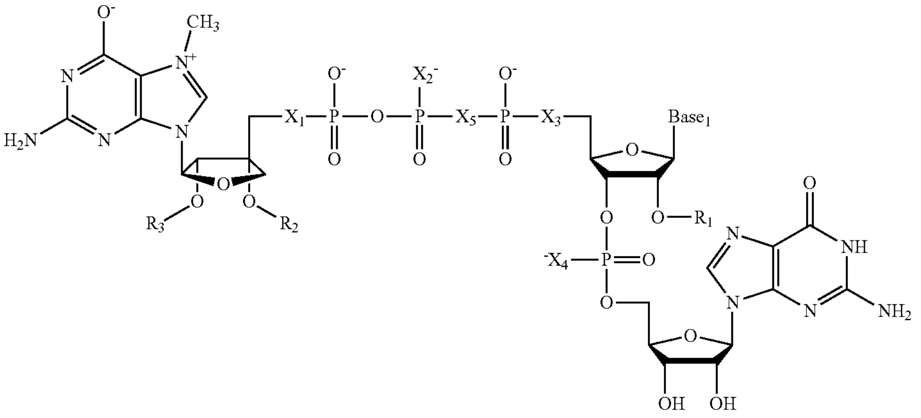

In which:

$R_1$, $R_2$, $R_3$ are selected from the group consisting of: H, $CH_3$, alkyl, wherein the substituents R with different numbers may be the same or different Base[1] is selected from a group with composition:

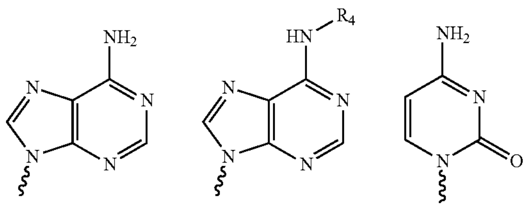

-continued

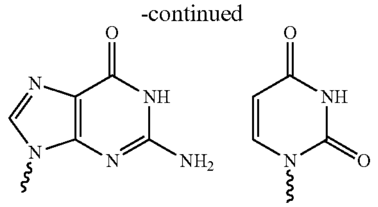

wherein $R^4$ is selected from the group consisting of: H, $CH_3$, alkyl, alkenyl, alkinyl, alkylaryl, $X_1$, $X_3$, are selected from the group of composition: O, S, Se, whereby substituents X with different numbers may be the same or different, $X_2$, $X_4$ are selected from the group consisting of: O, S, Se, $BH_3$, whereby the X substituents with different numbers may be the same or different, $X_5$ is selected from the group consisting of: O, $CH_2$, $CF_2$, $CCl_2$, at least one of the substituents among $X_1$, $X_2$, $X_3$, $X_4$, and $X_5$ is different from O, except for a compound in which:

$R_1$ stands for hydrogen or $CH_3$, $R_2$ stands for hydrogen, $R_3$ stands for $CH_3$, $X_1$, $X_3$, $X_4$, and $X_5$ stand for oxygen, $X_2$ stands for sulfur, and $Base_1$ stands for guanine.

Advantageously, in the compound according to the invention $R_2$ stands for OH, while $R_3$ stands for OH.

Advantageously, in the compound according to the invention $X_5$ stands for $CH_2$.

Advantageously, in the compound according to the invention $X_2$ means S.

Advantageously, in the compound according to the invention $X_3$ means S.

Advantageously, in the compound according to the invention $X_4$ means S.

Advantageously, the compound according to the invention is selected from the group consisting of:

compound $m^7Gpp_SpApG$ of formula:

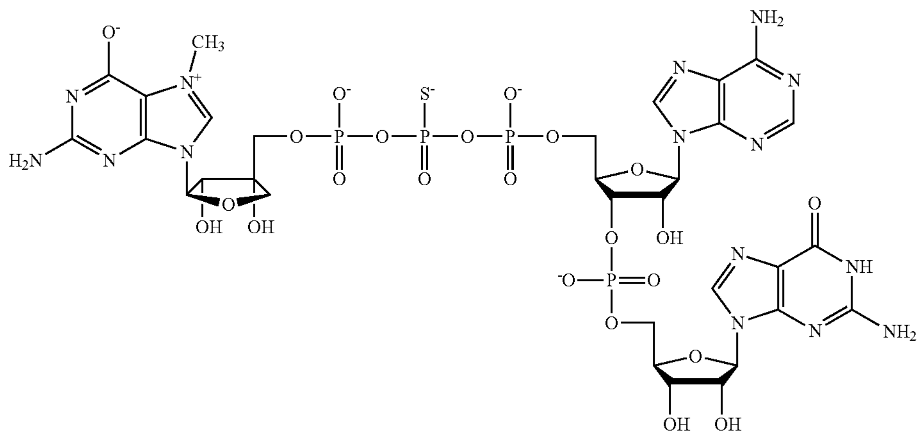

(D1 and D2)

compound $m^7Gpp_SpA_mpG$ of formula:

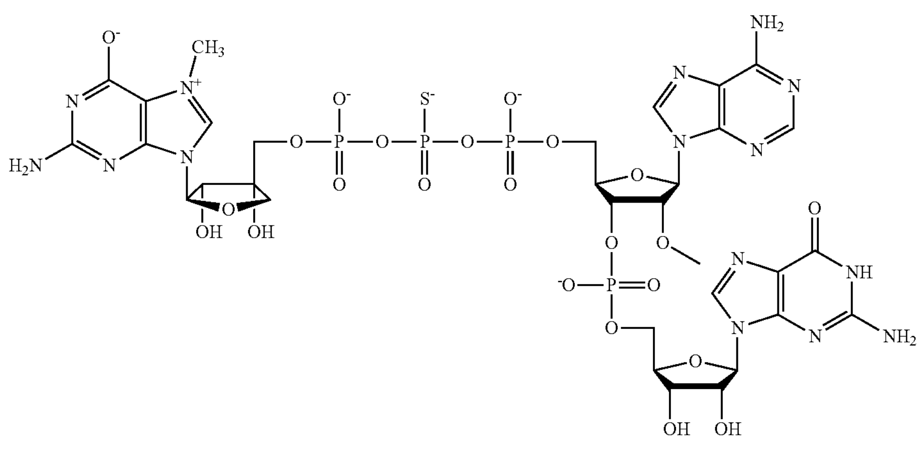

(D1 and D2)

compound $m^7Gpp_Sp^{m6}ApG$ of formula:
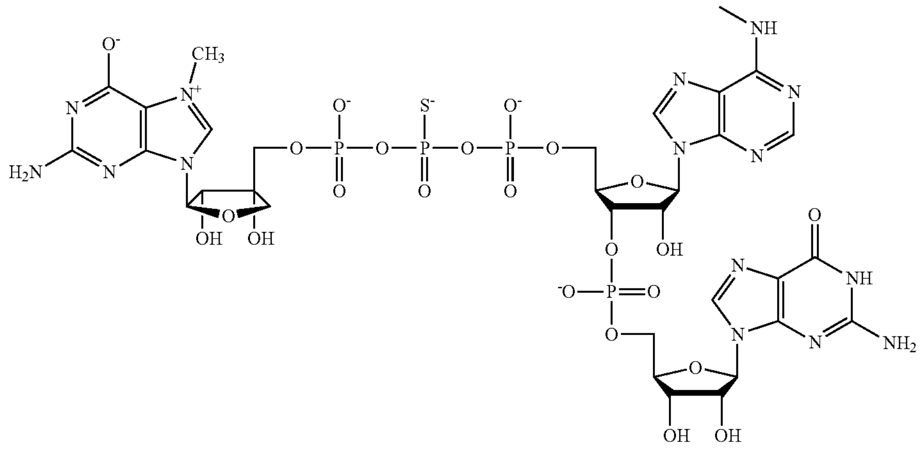
(D1 and D2)
compound $m^7Gpp_Sp^{m6}A_mpG$ of formula:
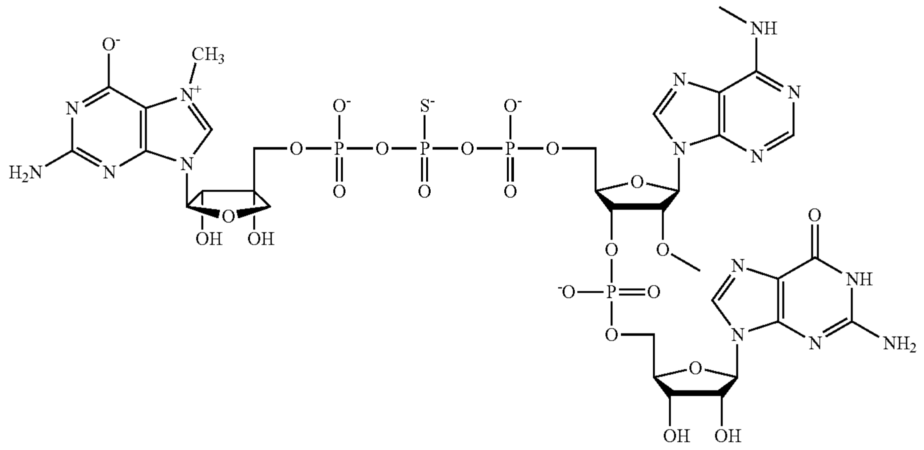
(D1 and D2)

compound $m^7GpppAp_SG$ of formula:
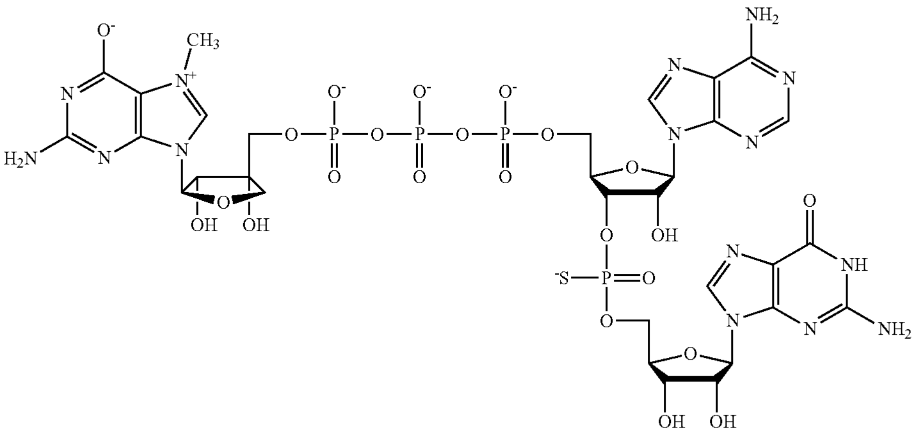
(D1 and D2)
compound $m^7Gppp5'SA_mpG$ of formula:
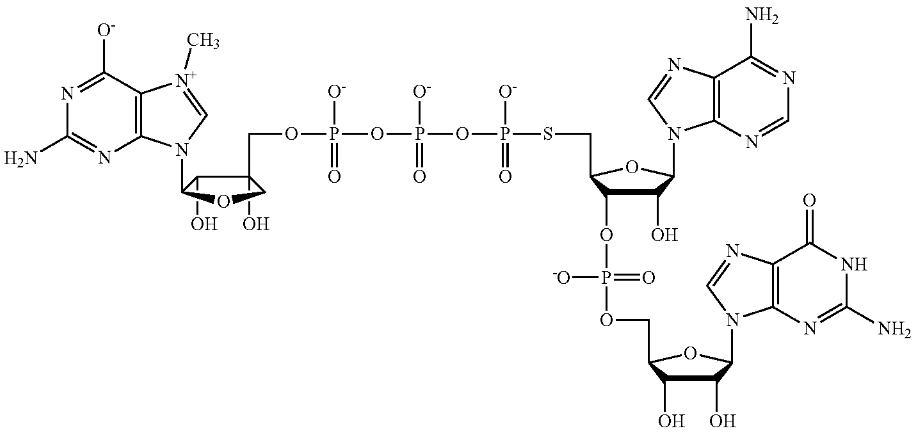
compound $m^7Gppp5'SA_mpG$ of formula:
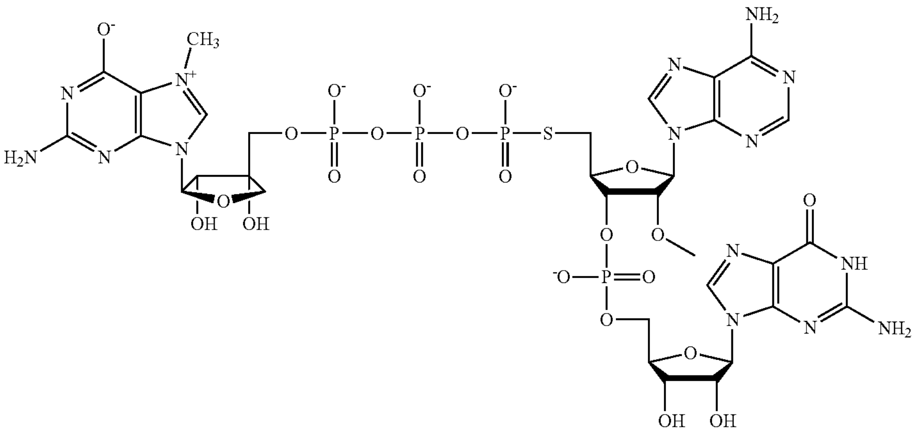

compound $m^7GppCH_2pApG$ of formula:
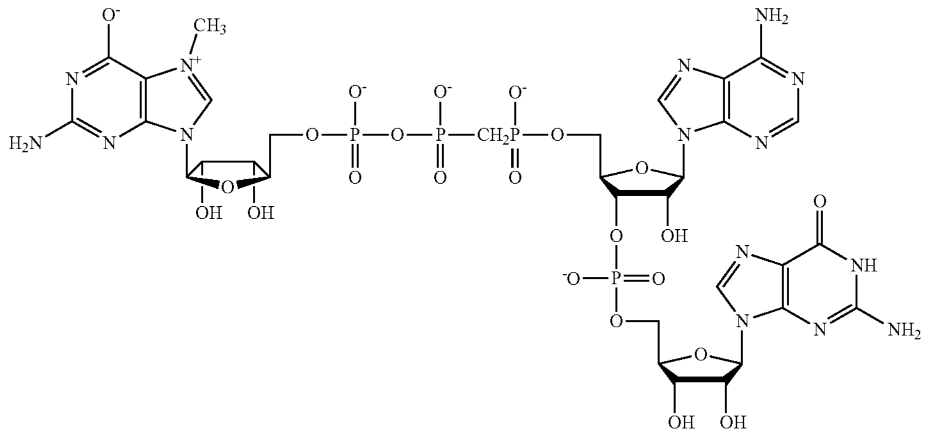
compound $m^7GppCH_2$ $pA_mpG$ of formula:
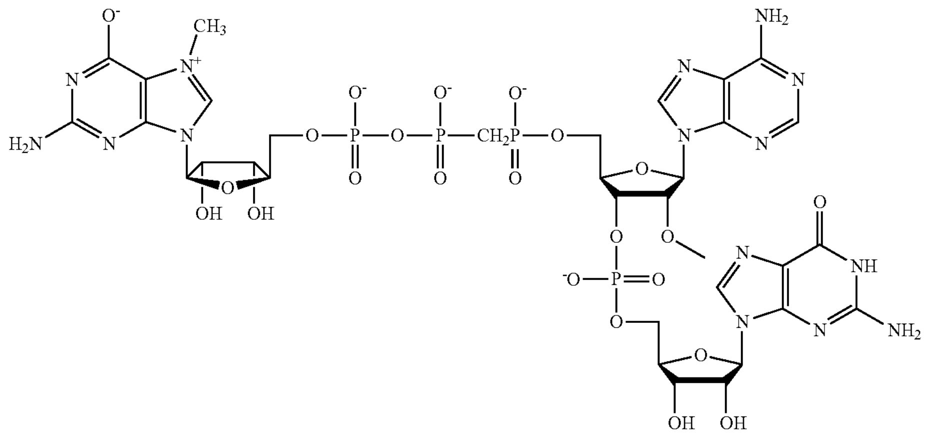
compound $m^7GppCH_2p^{m6}ApG$ of formula:
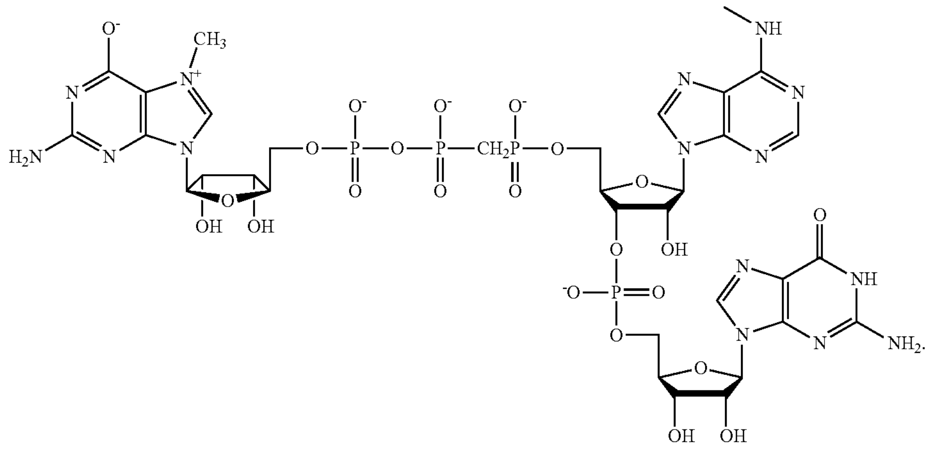

Preferably, the compound according to the invention consists essentially of a single stereoisomer or comprises a mixture of at least two stereoisomers, a first diastereoisomer and a second diastereoisomer, the diastereoisomers being identical except that they have different stereochemical configurations around a stereogenic phosphorus atom, said stereogenic phosphorus atom being bonded to a sulfur atom, a selenium atom, or a borane group.

Another embodiment of the invention is an RNA molecule which at the 5' end contains a compound according to the invention as defined above.

A further embodiment of the invention is a method for in vitro synthesis of an RNA molecule according to the invention as defined above, said method comprising reacting ATP, CTP, UTP and GTP, a compound according to the invention as defined above, and a polynucleotide template in the presence of an RNA polymerase, under conditions that allow the RNA polymerase to synthesize RNA copies on the polynucleotide template; wherein some of the RNA copies will contain a compound according to the invention as defined above, resulting in the production of an RNA molecule according to the invention.

Another embodiment of the invention is a method for synthesizing a protein or peptide in vitro, said method comprising translating an RNA molecule according to the invention as defined above in a cell-free protein synthesis system, the RNA molecule comprising an open reading frame, under conditions that allow translation from the open reading frame of the RNA molecule of a protein or peptide encoded by the open reading frame.

Another embodiment of the invention is a method for synthesizing a protein or peptide in vivo, characterized in that it comprises introducing an RNA molecule according to the invention as defined above into a cell, said RNA molecule comprising an open reading frame, under conditions that allow translation from the open reading frame of the RNA molecule with formation of a protein or peptide encoded by said open reading frame, said cell not being contained in the body of a patient.

Another embodiment of the invention is the use of a compound according to the invention defined above in the in-vitro synthesis of an RNA molecule.

Another embodiment of the invention is to use an RNA molecule according to the invention as defined above in the in-vitro synthesis of a protein or peptide.

Another embodiment of the invention is a compound according to the invention as defined above or an RNA molecule according to the invention as defined above for use in medicine, diagnostics or pharmacy.

DETAILED DESCRIPTION OF THE INVENTION

Surprisingly, it turned out that the tri-nucleotide analogs of the mRNA 5' end (cap) according to the invention enable obtaining mRNAs with higher capping efficiency and to obtain a higher level of expression of proteins encoded by these mRNAs compared to mRNAs obtained using the mRNA 5'-end (cap) analogues known in the art.

In addition, the invention enables the site-specific replacement of O by S or O by $CH_2$ or O by another atom or group of atoms in the 5',5'-triphosphate chain of the mRNA cap without the need for additional ARCA modifications (i.e. known methylations at the 2'-0 or 3'-0 position of 7-methylguanosine)[24,25] because the compounds proposed according to the invention incorporate into the obtained mRNA only in the correct orientation.

International application WO2019175356 discloses modified 5' trinucleotides for RNA capping. However, unlike the compounds described in this application, they have an ARCA-type modification within 7-methylguanosine. The presence of this unnatural modification raises the cost of cap synthesis and may have negative consequences in vivo, e.g., as a result of slower cap degradation by the enzyme DcpS, especially in combination with certain triphosphate bridge modifications[26]. This may result in the accumulation of the cap in the cell, which in therapeutic applications may induce reduced mRNA expression efficiency and, in case of high doses or repeated administration, even toxicity. Thus, compounds according to the invention in which $R_2$=OH and $R_3$=OH are particularly preferable.

The invention enables also the site-specific replacement of O by S in the structure of the first phosphodiester bond at the 5' end of the mRNA. Replacement of O by S in the structure of the first phosphodiester bond in mRNA allows for a higher level of expression of proteins encoded by such mRNA compared to mRNA obtained using cap art analogues known in the art, especially if the mRNA used has not been subjected to prior enzymatic treatment to remove uncapped mRNA.

Furthermore, the invention enables several modifications to be carried out simultaneously, in particular 0 by S replacement in the triphosphate chain or in the structure of the first phosphodiester bond together with the introduction of natural epigenetic modifications at the 5' end of mRNA such as 2'-O-methylation of the first transcribed nucleotide and N6-methylation of adenosine.

It has also surprisingly been found that the presence of a particular phosphate modification in a trinucleotide according to the invention may have a different effect on the properties of the molecule than the presence of the same modification in a dinucleotide known from the state of the art. For example, it has been found that cap analogs according to the invention having O to $CH_2$ substitutions enable obtaining in vitro transcribed mRNA characterized by a higher expression level of proteins encoded by such mRNA compared to mRNA obtained using prior art trinucleotide cap analogs. Earlier studies have shown that the replacement of O by $CH_2$ in the triphosphate bridge of mRNA cap obtained using prior art dinucleotide cap analogs (compound $m_2^{7,3'\text{-}O}GppCH_2pG$) results in a significant reduction in protein expression compared to mRNA obtained using prior art cap analogs not carrying an O by $CH_2$ substitution (compound $m_2^{7,3'\text{-}O}GpppG$).[10] Furthermore, mRNAs modified with trinucleotide cap analogs according to the invention having O to $CH_2$ substitutions at the $X_5$ position or O to S substitutions at the $X_2$ position ($m^7GppCH_2pAmpG$ and $m^7Gpp_SpA_mpG$ D2, respectively) had very similar translational properties, while the respective dinucleotides ($m_2^{7,3'\text{-}O}GppCH_2pG$ and $m_2^{7,2'\text{-}O}Gpp_SpG$ D2, respectively) have opposite effects on translational properties (the former decreases and the latter increases translation efficiency relative to the compound without modification)[25,8]. This means that the observations for dinucleotides are not directly applicable to trinucleotides.

It has also surprisingly been found that the cap analogs according to the invention carrying an O by $CH_2$ or O by S substitution enable the production of in vitro transcribed mRNA with a higher capping yield than the capping yield obtained with dinucleotide cap analogues containing the same modifications and used at the same concentrations.

Cap analogs of the invention enable efficient preparation of in vitro transcribed mRNA containing any nucleobase within the nucleotide present at the first transcribed nucleotide position [in contrast to known dinucleotide cap analogs, which due to limitations of the sequences used for in in vitro transcription with most viral polymerases (T7, SP6) are only suitable for purine incorporation].

The publications cited in the description and the references given therein are hereby incorporated as references.

BRIEF DESCRIPTION OF THE FIGURES

For a better understanding of the invention, it has been illustrated in the working examples and the attached drawings, in which.

Figure 1:
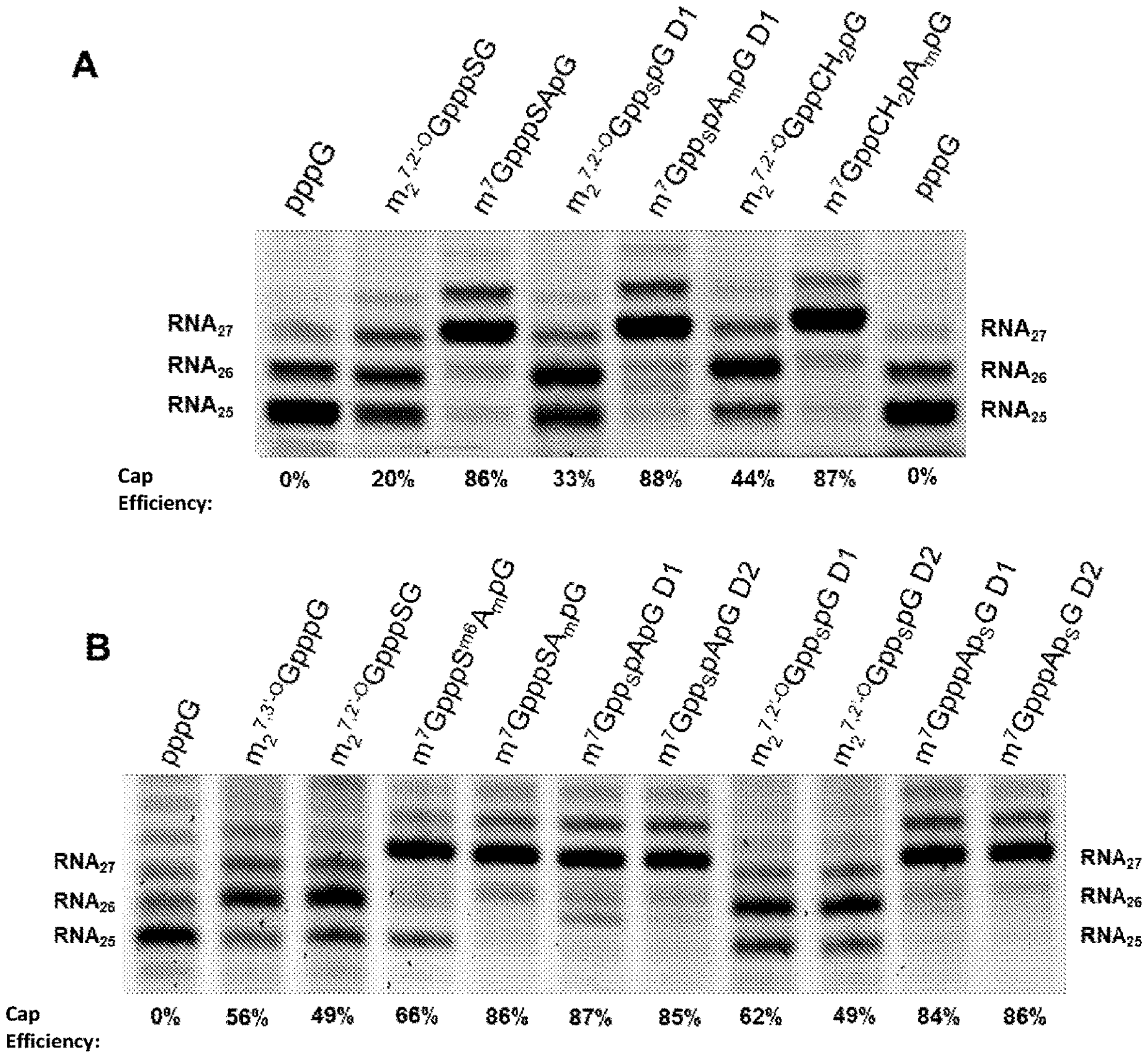
FIGS. 1 A and B presents an analysis of the capping efficiency for RNAs obtained using selected tri-nucleotide cap analogs according to the invention (used in a 6-fold excess over GTP) or dinucleotide cap analogs known in the art (also used in a 6-fold excess over GTP).

The term "alkyl" refers to a saturated, linear or branched hydrocarbon substituent with the indicated number of carbon atoms, preferably from 1 to 10 carbon atoms. Examples of the alkyl substituent are -methyl, -ethyl, -n-propyl, -n-butyl, -n-pentyl, -n-hexyl, -n-heptyl, -n-octyl, -n-nonyl, and -n-decyl. Representative branched-(C1-C10) alkyls include -isopropyl, -sec-butyl, -isobutyl, -tert-butyl, -isopentyl, -neopentyl, -1-methylbutyl, -2-methylbutyl, -3-methylbutyl, -1,1-dimethylpropyl, -1,2-dimethylpropyl, -1-methylpentyl, -2-methylpentyl, -3-methylpentyl, -4-methylpentyl, -1-ethylbutyl, -2-ethylbutyl, -3-ethylbutyl, -1,1-dimethylbutyl, -1,2-dimethylbutyl, 1,3-dimethylbutyl, -2,2-dimethylbutyl, -2,3-dimethylbutyl, -3,3-dimethylbutyl, -1-methylhexyl, 2-methylhexyl, -3-methylhexyl, -4-methylhexyl, -5-methylhexyl, -1,2-dimethylpentyl, -1,3-dimethylpentyl, -1,2-dimethylhexyl, -1,3-dimethylhexyl, -3,3-dimethylhexyl, 1,2-dimethylheptyl, -1,3-dimethylheptyl, and -3,3-dimethylheptyl and the like.

The term "alkenyl" refers to a saturated, linear or branched non-cyclic hydrocarbon substituent with the indicated number of carbon atoms and containing at least one carbon-carbon double bond. Examples of the alkenyl substituent are -vinyl, -allyl, -1-butenyl, -2-butenyl, -isobutyleneyl, -1-pentenyl, -2-pentenyl, -3-methyl-1-butenyl, -2-methyl-2-butenyl, -isoprenyl, -2,3-di-methyl-2-butenyl, -1-hexenyl, -2-hexenyl, -3-hexenyl, -1-heptenyl, -2-heptenyl, -3-heptenyl, -1-octetyl, -2-octenyl, -3-octenyl, -1-nonenyl, -2-nonenyl, -3-nonenyl, -1-decenyl, -2-decenyl, -3-decenyl and the like.

The term "alkynyl" refers to a saturated, linear or branched non-cyclic hydrocarbon substituent with the indicated number of carbon atoms and containing at least one carbon-carbon triple bond. Examples of the alkynyl substituent are acetylenyl, propynyl, -1-butynyl, -2-butynyl, -1-pentynyl, -2-pentynyl, -3-methyl-1-butynyl, 4-pentynyl, -1-hexynyl, -2-hexynyl, -5-hexinyl and the like.

The term "aryl" refers to an unsaturated, ring, aromatic or heteroaromatic (i.e. containing a heteroatom instead of carbon) substituent hydrocarbon having the indicated number of carbon atoms, preferably from 6 to 10 carbon atoms. Examples of aryl are: phenyl, naphthyl, anthracyl, phenanthryl.

The term "alkylaryl" refers to an unsaturated hydrocarbon substituent constructed from an alkyl and aryl portion attached together (as defined above). Examples of alkylaryl are benzyl, phenylethyl, phenylpropyl, naphthylmethyl, naphthylethyl, etc.

The term "heteroatom" means an atom selected from the group oxygen, sulfur, nitrogen, phosphorus and others.

The term "HPLC" means high performance liquid chromatography, and the solvents designated as solvents for "HPLC" mean solvents of adequate purity for HPLC (High Performance Liquid Chromatography) analysis.

The term "NMR" means Nuclear Magnetic Resonance.

The term "HRMS" means High Resolution Mass Spectrometry

WAYS OF IMPLEMENTING THE INVENTION

The following examples are provided solely to illustrate the invention and to clarify its particular aspects, and not to limit it and should not be equated with its entire scope as defined in the appended claims. In the examples below, unless otherwise indicated, standard materials and methods used in the field were used or manufacturer's recommendations for specific materials and methods were followed.

EXAMPLES

The trinucleotide cap analogs were synthesized by combining solid supported synthesis and solution phase synthesis methods, followed by isolation of the compounds using a two step purification process. The starting point was the synthesis of dinucleotides (5'-monophosphates pNpG; 5'-tioesters $p^{5'S}NpG$, 5'-methylenebisphosphonates $pCH_2pNpG$, and dinucleotides with 3',5'-phosphorothioate bonds pNpsG). The 3',5'-phosphorothioate linkage was formed by using DDTT [((dimethylamino-methylidene) amino)-3H-1,2,4-dithiazoline-3-thione] for oxidation of the phosphoramidite. Dinucleotides were cleaved off from the support, deprotected, and isolated by ion-exchange chromatography as triethylammonium salts, which were suitable for $ZnCl_2$-mediated coupling reactions.

$p^{5'S}NpG$ and pNpsG dinucleotides were subjected to coupling reaction with $m^7$GDP-Im[15] to afford analogs of $m^7Gppp^{5'S}NpG$ oraz $m^7GpppNp_SG$ type, respectively, whereas $pCH_2pNpG$ dinucleotides were subjected to coupling reaction with $m^7$GMP-Im[15] to afford analogs of $m^7GppCH_2pNpG$ type. The synthesis of analogs carrying β-thiophosphate moiety required activation of the dinucleotide 5'-phosphates into corresponding P-imidazolides, which were subsequently coupled with $m^7$GDP-β-S[15]. All compounds were isolated by ion-exchange chromatography and additionally purified by RP HPLC, to afford ammonium salts suitable for biological studies. In the case of analogs carrying β-thiophosphate or 3',5'-phosphorothioate, diastereomers of the compounds were separated during RP HPLC purification step and marked D1 and D2 according to the elution order. Other trinucleotides modified within the triphosphate bridge according to the invention can be obtained using the synthetic strategies described in Examples 1-8 in combination with methods for introducing suitable phosphate bridge modifications described in the literature for dinucleotide cap analogs.[26,27,28,29,30]

Example 1: Synthesis of 5'-Phosphorylated Dinucleotides (pNpG)

Synthesis of dinucleotides was performed using ÄKTA Oligopilot plus 10 synthesizer (GE Healthcare) on a 5'-O-DMT-2'-O-TBDMS-$rG^{iBu}$ 3'-Icaa PrimerSupport 5G (308 μmol/g) solid support (GE Healthcare). In the coupling step, 2.0 equivalents of 5'-O-DMT-2'-O-TBDMS/2'-O-Me-3'-O-phosphoramidite ($rA^{Ac}$, $rA_m^{Pac}$, $^{m6}A^{Ac}$ or $^{m6}A_m^{Pac}$)[12] or biscyanoethyl phosphoramidite and 0.30 M 5-(benzylthio)-1-H-tetrazole in acetonitrile were recirculated through the column for 15 min. A solution of 3% (v/v) dichloroacetic acid in toluene was used as a detritylation reagent and 0.05 M iodine in pyridine/water (9:1) for oxidation, 20% (v/v) N-methylimidazole in acetonitrile as Cap A and a mixture of 40% (v/v) acetic anhydride and 40% (v/v) pyridine in acetonitrile as Cap B. After the last cycle of synthesis, RNAs, still on the solid support, were treated with 20% (v/v) diethylamine in acetonitrile to remove 2-cyanoethyl protecting groups. Finally, the solid support was washed with acetonitrile and dried with argon. The product was cleaved from the solid support and deprotected with AMA (40% methylamine/33% ammonium hydroxide $1:1_{v/v}$; 55° C., 1 h), evaporated to dryness and redissolved in DMSO (200 μL). The TBDMS groups were removed using triethylammonium trihydrofluoride (TEA·3HF; 250 μL, 65° C., 3 h), and then the mixture was cooled down and diluted with 0.25 M $NaHCO_3$ in water (20 mL). The product was isolated by ion-exchange chromatography on DEAE Sephadex (gradient elution 0-0.9 M TEAB) to afford after evaporation triethylammonium salt of pNpG dinucleotide. The yield was estimated by UV absorption at 260 nm, assuming the extinction coefficient ε=27.1 L/mmol/cm)

| Compound | Synthesis scale [a] [μmol] | Yield [$mOD_{260\ nm}$] | Yield [μmol] | RP HPLC [b] $R_t$ [min] | m/z $_{calcd.}$ | m/z $_{found}$ |
|---|---|---|---|---|---|---|
| pApG | 25 | 530 | 19.6 | 8.680 | 691.10324 | 691.10392 |
| $pA_mpG$ | 4 × 50 | 3840 | 141.7 | 12.070 | 705.11889 | 705.11981 |
| $p^{m6}ApG$ | 25 | 328 | 12.1 | 11.179 | 705.11889 | 705.11820 |
| $p^{m6}A_mpG$ | 2 × 50 | 1645 | 60.7 | 14.434 | 719.13454 | 719.13537 |

[a] calculated as a product of solid support weight and loading;
[b] Linear gradient elution: 0-50% MeOH in $CH_3COONH_4$ pH 5.9 in 30 min $p(m^6A_m)pG$: $^1H$ NMR (500 MHz, $D_2O$, 25° C.): δ=8.37 (s, 1H, $H8_A$), 8.14 (s, 1H, $H2_A$), 7.89 (s, 1H, $H8_G$), 6.09 (d, $^3J_{H,H}$=4.4 Hz, 1H, $H1'_A$), 5.81 (d, $^3J_{H,H}$=5.1 Hz, 1H, $H1'_G$), 4.91 (m, 1H, $H3'_A$), 4.68 (dd, $^3J_{H,H}$=5.1 Hz, $^3J_{H,H}$=5.1 Hz, 1H, $H2'_G$), 4.48-4.43 (m, 3H, $H2'_A$, $H4'_A$, $H3'_G$), 4.34 (m, 1H, $H4'_G$), 4.25-4.08 (m, 4H, $H5'_A$, $H5''_A$, $H5'_G$, $H5''_G$), 3.53 (s, 3H, 2'-O—$CH_3$), 3.46 (q, $^3J_{H,H}$=7.3 Hz, 18H, $CH_{2[TEAH+]}$), 3.09 (s, overlapped with TEAH*, $N^6$—$CH_3$), 1.31 (t, $^3J_{H,H}$=7.3 Hz, 27H, $CH_{3[TEAH+]}$) ppm; $^{31}P$ NMR (202.5 MHz, $D_2O$, $H_3PO_4$, 25° C.): δ=1.1 (s, 1P, $P_A$), 0.0 (s, 1P, $P_G$) ppm;

Example 2: Synthesis of Dinucleotide 3',5'-Thiophosphodiester ($pAp_SG$)

The synthesis was performed in 25 μmol scale using ÄKTA Oligopilot plus 10 synthesizer (GE Healthcare) on a 5'-O-DMT-2'-O-TBDMS-$rG^{iBu}$ 3'-Icaa PrimerSupport 5G (308 μmol/g) solid support (GE Healthcare). In the coupling step, 5.0 equivalents of 5'-O-DMT-2'-O-TBDMS-$rA^{Ac}$ 3'-O-phosphoramidite or biscyanoethyl phosphoramidite and 0.30 M 5-(benzylthio)-1-H-tetrazole in acetonitrile were recirculated through the column for 15 min. A solution of 3% (v/v) dichloroacetic acid in toluene was used as a detritylation reagent, 20% (v/v) N-methylimidazole in acetonitrile as Cap A and a mixture of 40% (v/v) acetic anhydride and 40% (v/v) pyridine in acetonitrile as Cap B. Oxidation to phosphorothioate was performed using ((dimethylamino-methylidene)amino)-3H-1,2,4-dithiazoline-3-thione (DDTT) and oxidation to 5'-phosphate was performed using 0.05 M iodine in pyridine/water (9:1). After the last cycle of synthesis, RNAs, still on the solid support, were treated with 20% (v/v) diethylamine in acetonitrile to remove 2-cyanoethyl protecting groups. Finally, the solid support was washed with acetonitrile and dried with argon. The product was cleaved from the solid support and deprotected with AMA (40% methylamine/33% ammonium hydroxide $1:1_{v/v}$; 55° C., 1 h), evaporated to dryness and redissolved in DMSO (200 μL). The TBDMS groups were removed using triethylammonium trihydrofluoride (TEA·3HF; 250 μL, 65° C., 3 h), and then the mixture was cooled down and diluted with 0.25 M $NaHCO_3$ in water (20 mL). The product was isolated by ion-exchange chromatography on DEAE Sephadex (gradient elution 0-0.9 M TEAB) to afford after evaporation triethylammonium salt of $pAp_SG$ (395 $mOD_{260\ nm}$, 14.6 μmol) as a mixture of two diastereomers in ca. 2:3 ratio.

$pAp_SG$ D1: RP-HPLC: $R_t$=11.012 min*; HRMS ESI(−): m/z 707.08078 (calcd. for $C_{20}H_{25}N_{10}O_{13}P_2S^-$ $[M-H]^-$ 707.08040);

$pAp_SG$ D2: RP-HPLC: $R_t$=11.179 min*; HRMS ESI(−): m/z 707.08088 (calcd. for $C_{20}H_{25}N_{10}O_{13}P_2S^-$ $[M-H]^-$ 707.08040);

* Linear gradient elution: 0-50% MeOH in $CH_3COONH_4$ pH 5.9 in 30 min

Example 3: Synthesis of Dinucleotide 5'-Phosphorothiolates ($p^{5'S}ApG$ and $p^{5'S}A_mpG$)

Synthesis of 5'-OH-NpG dinucleotides was performed in 50 μmol scale using ÄKTA Oligopilot plus 10 synthesizer (GE Healthcare) on a 5'-O-DMT-2'-O-TBDMS-$rG^{iBu}$ 3'-Icaa PrimerSupport 5G (308 μmol/g) solid support (GE Healthcare). In the coupling step, 2.5 equivalents of adenosine 3'-0-phosphoramidite (5'-O-DMT-2'-O-PivOM-$rA^{Pac}$ or 5'-O-DMT-$rA_m^{Pac}$) and 0.30 M 5-(benzylthio)-1-H-tetrazole in acetonitrile were recirculated through the column for 15 min. A solution of 3% (v/v) dichloroacetic acid in toluene was used as a detritylation reagent and 0.05 M iodine in pyridine/water (9:1) for oxidation, 20% (v/v) N-methylimidazole in acetonitrile as Cap A and a mixture of 40% (v/v) acetic anhydride and 40% (v/v) pyridine in acetonitrile as Cap B. After the last cycle of synthesis, the support was treated with 20% (v/v) diethylamine in acetonitrile to remove 2-cyanoethyl protecting groups, washed with acetonitrile and dried with argon.

Dinucleotide, still on a solid support, was then converted into 5'-iodo derivative by pushing back and forth (using two syringes attached to the column) a solution of methyltriphenoxyphosphonium iodide (1.5 g) in DMF (5 mL) for 15 minutes. The resin was then washed with DMF (10 mL) and acetonitrile (10 ml), dried and transferred to a flask containing a solution of triethylammonium thiophosphate (ca. 0.16 M) and triethylamine (0.64 M) in DMF (1 mL). The slurry was stirred at 4° C. overnight, filtered and washed with acetonitrile. The product was cleaved and deprotected using AMA (40% methylamine/33% ammonium hydroxide 1:$1_{v/v}$; 55° C., 1 h) and isolated by ion-exchange chromatography on DEAE Sephadex (gradient elution 0-0.9 M TEAB) to afford after evaporation triethylammonium salt of $p^{5'S}$NpG dinucleotide.

| Compound | Synthesis scale [a] [μmol] | Yield [$mOD_{260\ nm}$] | Yield [μmol] | RP HPLC [b] $R_t$ [min] | m/z $_{calcd.}$ | m/z $_{found}$ |
|---|---|---|---|---|---|---|
| $p^{5'S}$ApG | 50 | 430 | 15.9 | 6.497** | 707.08040 | 707.08101 |
| $p^{5'S}A_m$pG | 50 | 285 | 10.5 | 11.398* | 721.09605 | 721.09686 |

[a] calculated as a product of solid support weight and loading;
[b] Linear gradient elution: 0-50% MeOH in $CH_3COONH_4$ pH 5.9 in 30 min (*) or 15 min (**)

Example 4: Synthesis of Dinucleotide 5'-Methylenebisphosphonates ($pCH_2$pApG, $pCH_2pA_m$pG and $pCH_2p^{m6}$ApG)

Synthesis of 5'-OH-NpG dinucleotides was performed using ÄKTA Oligopilot plus 10 synthesizer (GE Healthcare) on a 5'-O-DMT-2'-O-TBDMS-$rG^{iBu}$ 3'-Icaa PrimerSupport 5G (308 μmol/g) solid support (GE Healthcare). In the coupling step, 5.0 equivalents of 5'-O-DMT-2'-O-TBDMS/2'-O-Me-3'-O-phosphoramidite ($rA^{Ac}$, $rA_m{}^{Pac}$ or $^{m6}A^{Ac}$) and 0.30 M 5-(benzylthio)-1-H-tetrazole in acetonitrile were recirculated through the column for 15 min. A solution of 3% (v/v) dichloroacetic acid in toluene was used as a detritilation reagent and 0.05 M iodine in pyridine/water (9:1) for oxidation, 20% (v/v) N-methylimidazole in acetonitrile as Cap A and a mixture of 40% (v/v) acetic anhydride and 40% (v/v) pyridine in acetonitrile as Cap B. After the synthesis, the support was washed with acetonitrile and dried with argon. A solution of methylenebis(phosphonic dichloride) (500 mg, 2 mmol) in trimethyl phosphate (5 mL) cooled to −18° C. was applied to the column and left at 2° C. for 7 hours. Then the solution was removed and the support was washed with trimethyl phosphate (5 mL) and acetonitrile (10 mL) and dried with argon. The column was washed with 5 mL of 0.9 M TEAB and the resin was incubated with fresh portion of TEAB at 2° C. overnight. The product was cleaved from the solid support and deprotected with AMA (40% methylamine/33% ammonium hydroxide 1:$1_{v/v}$; 55° C., 1 h), evaporated to dryness and redissolved in DMSO (200 μL). The TBDMS groups were removed using triethylammonium trihydrofluoride (TEA·3HF; 250 μL, 65° C., 3 h), and then the mixture was cooled down, diluted with water and pH was adjusted to 1 using hydrogen chloride and left for 7 days at room temperature to hydrolyze fluorobisphosphonate. The product was isolated by ion-exchange chromatography on DEAE Sephadex (gradient elution 0-0.9 M TEAB) to afford after evaporation triethylammonium salt of $pCH_2$pNpG dinucleotide.

| Compound | Synthesis scale [a] [μmol] | Yield [$mOD_{260\ nm}$] | Yield [μmol] | RP HPLC [b] $R_t$ [min] | m/z $_{calcd.}$ | m/z $_{found}$ |
|---|---|---|---|---|---|---|
| $pCH_2$pApG | 25 | 118 | 4.35 | 7.200 | 769.09031 | 769.09100 |
| $pCH_2pA_m$pG | 50 | 345 | 12.7 | 9.728 | 783.10596 | 783.10695 |
| $pCH_2p^{m6}$ApG | 25 | 238 | 8.78 | 9.008 | 783.10596 | 783.10690 |

[a] calculated as a product of solid support weight and loading;
[b] Linear gradient elution: 0-50% MeOH in $CH_3COONH_4$ pH 5.9 in 30 min $pCH_2pApG$: RP-HPLC: $R_t$=7.200 min; $^1H$ NMR (500 MHz, $D_2O$, 25° C.): δ=8.57 (s, 1H, $H8_A$), 8.28 (s, 1H, $H2_A$), 8.03 (s, 1H, $H8_G$), 6.02 (d, $^3J_{H,H}$=4.7 Hz, 1H, $H1'_A$), 5.84 (d, $^3J_{H,H}$=5.2 Hz, 1H, $H1'_G$), 4.84-4.80 (m, overlapped with HDO, 1H, $H3'_A$), 4.79 (m, overlapped with HDO, 1H, $H2'_A$) 4.74 (dd, $^3J_{H,H}$=5.2 Hz, $^3J_{H,H}$≈5.2 Hz, 1H, $H2'_G$), 4.49 (m, 2H, $H4'_A$, $H3'_G$), 4.34 (m, 1H, $H4'_G$), 4.27 (m, 1H, $H5'_G$), 4.21-4.12 (m, 3H, $H5''_G$, $H5'_A$, $H5''_A$), 3.20 (q, $^3J_{H,H}$=7.3 Hz, 1.5H, $CH_{2[TEAH+]}$), 2.21 (t, $^2J_{H,P}$=18.9 Hz, 2H, P—$CH_2$—P), 1.28 (t, $^3J_{H,H}$=7.3 Hz, 2.25H, $CH_{3[TEAH+]}$) ppm; $^{31}P$ NMR (202.5 MHz, $D_2O$, $H_3PO_4$, 25° C.): δ=19.1 (m, 1P, $P_\alpha$), 16.1 (m, 1P, $P_\rho$), 0.3 (s, 1P, $P_G$) ppm; HRMS ESI(−): m/z 769.09100 (calcd. for $C_{21}H_{28}N_{10}O_{16}P_3$ $[M-H]^-$ 769.09031);

$pCH_2p(m^6{}_A)pG$: RP-HPLC: $R_t$=9.008 min; $^1H$ NMR (500 MHz, $D_2O$, 25° C.): δ=8.42 (s, 1H, $H8_A$), 8.16 (s, 1H, $H2_A$), 7.89 (s, 1H, $H8_G$), 5.99 (d, $^3J_{H,H}$=3.6 Hz, 1H, $H1'_A$), 5.80 (d, $^3J_{H,H}$=5.1 Hz, 1H, $H1'_G$), 4.84-4.76 (m, overlapped with HDO, 2H, $H3'_A$, $H2'_A$), 4.66 (dd, $^3J_{H,H}$=5.1 Hz, $^3J_{H,H}$=5.1 Hz, 1H, $H2'_G$), 4.49 (m, 1H, $H4'_A$), 4.46 (m, 1H, $H3'_G$), 4.35-4.48 (m, 2H, $H4'_G$, $H5'_G$), 4.22-4.11 (m, 3H, $H5''_G$, $H5'_A$, $H5''_A$), 2.80 (s, 3H, $N^6$—$CH_3$), 2.20 (t, $^2J_{H,P}$=19.7 Hz, 2H, P—$CH_2$—P) ppm; $^{31}P$ NMR (202.5 MHz, D20, $H_3PO_4$, 25° C.): δ=19.2 (m, 1P, $P_\alpha$), 15.8 (td, $^2J_{P,H}$=19.7 Hz, $^2J_{P,P}$=9.1 Hz, 1P, $P_\beta$), 0.3 (s, 1P, $P_G$) ppm; HRMS ESI(−): m/z 783.10690 (calcd. for $C_{22}H_{30}N_{10}O_{16}P_3^-$ $[M-H]^-$ 783.10596);

Example 5: Synthesis of β-Phosphorothioate Tri-nucleotide Cap Analogs ($m^7Gpp_SpApG$ D1 and D2, $m^7Gpp_SpA_mpG$ D1 and D2, $m^7Gpp_Spm^6ApG$ D1 and D2, $m^7Gpp_Spm^6A_mpG$ D1 and D2)

Step 1. Activation of pNpG: Dinucleotide 5'-phosphate was dissolved in DMF (to obtain a 0.05 M solution) followed by addition of imidazole (16 equivalents), 2,2'-dithiodipiridine (6 equivalents), triethylamine (3 equivalents) and triphenylphosphine (6 equivalents). The mixture was stirred at room temperature for 48 h. The product was precipitated by addition of a solution of sodium perchlorate (10 equivalents) in acetonitrile (10 times the volume of DMF). The precipitate was centrifuged at 4° C., washed with cold acetonitrile 3 times and dried under reduced pressure to give a sodium salt of dinucleotide P-imidazolide (Im-pNpG).

Step 2. Formation of triphosphate bridge: 7-Methyl-guanosine p-thiodiphosphate ($m_7GDP$-β-S; obtained as described earlier and stored in TEAB at −20° C.)[15] was evaporated to an oil and redissolved in DMF (to obtain a 0.05 M solution). Then $ZnCl_2$ (8 equivalents) and Im-pNpG (0.5 equivalent) were added and the mixture was stirred at room temperature for 2 h. The reaction was quenched by addition of a solution of $Na_2EDTA$ (20 mg/mL; 8 equivalents) and $NaHCO_3$ (10 mg/mL) in water and the product was isolated by ion-exchange chromatography on DEAE Sephadex (gradient elution 0-1.2 M TEAB) to afford after evaporation triethylammonium salt of $m^7Gpp_SpNpG$. The diastereomers were separated by RP HPLC (C18) using a linear gradient of acetonitrile in aqueous $CH_3COONH_4$ buffer pH 5.9 to give after repeated freeze-drying from water ammonium salts of single diastereomers of $m^7Gpp_SpNpG$.

| Compound | Synthesis scale [a] [μmol] | Yield [b] [μmol] | RP HPLC [c] $R_t$ [min] | $m/z_{calcd.}$ | $m/z_{found}$ |
|---|---|---|---|---|---|
| $m^7Gpp_SpApG$ | 4.65 | D1: 0.81 | 8.705 | 1146.10981 | 1146.11096 |
| | | D2: 1.17 | 9.045 | | 1146.11147 |
| $m^7Gpp_SpA_mpG$ | 33.0 | D1: 6.50 | 10.493 | 1160.12546 | 1160.12689 |
| | | D2: 6.16 | 10.713 | | 1160.12696 |
| $m^7Gpp_Sp^{m6}ApG$ | 12.1 | D1: 0.10 | 9.886 | 1160.12546 | 1160.12714 |
| | | D2: 0.20 | 10.188 | | 1160.12748 |
| $m^7Gpp_Sp^{m6}A_mpG$ | 30.4 | D1: 7.06 | 12.225 | 1174.14111 | 1174.14244 |
| | | D2: 5.94 | 12.372 | | 1174.14250 |

[a] based on the amount of pNpG used for the synthesis;
[b] after RP HPLC;
[c] Linear gradient elution: 0-50% MeOH in $CH_3COONH_4$ pH 5.9 in 30 min

Example 6: Synthesis of Thiophosphodiester Tri-nucleotide Cap Analog ($m^7GpppAp_SG$ D1 and D2)

Dinucleotide $pAp_SG$ (197 mOD, 7.27 μmol), 7-methyl-guanosine-5'-diphosphate $P^2$-imidazolide $m^7GDP$-Im[15] (10.0 mg, 18.2 μmol) and $ZnCl_2$ (19.8 mg, 145 μmol) were dissolved in DMSO (145 μL) and the mixture was stirred at room temperature for 24 h. The reaction was quenched by addition of a solution of $Na_2EDTA$ (54 mg, 145 μmol) and $NaHCO_3$ (27 mg, 321 μmol) in water (2.7 mL) and the product was isolated by ion-exchange chromatography on DEAE Sephadex (gradient elution 0-1.2 M TEAB) to afford after evaporation triethylammonium salt of $m^7GpppAp_SG$. The diastereomers were separated by RP HPLC (C18) using a linear gradient of acetonitrile in aqueous $CH_3COONH_4$ buffer pH 5.9 to give after repeated freeze-drying from water ammonium salts of single diastereomers of $m^7GpppAp_SG$ (D1: 42.5 mOD, 1.33 μmol; D2: 77.0 mOD, 2.41 μmol).

$m^7GpppAp_SG$ D1: RP-HPLC: $R_t$=8.974 min*; HRMS ESI(−): m/z 1146.11093 (calcd. for $C_{31}H_{40}N_{15}O_{23}P_4S$ $[M-H]^-$ 1146.10981);

$m^7GpppAp_SG$ D2: RP-HPLC: $R_t$=9.662 min*; HRMS ESI(−): m/z 1146.11137 (calcd. for $C_{31}H_{40}N_{15}O_{23}P_4S$ $[M-H]^-$ 1146.10981);

* Linear gradient elution: 0-50% MeOH in $CH_3COONH_4$ pH 5.9 in 30 min

Example 7: Synthesis of 5'-Phosphorothiolate Tri-nucleotide Cap Analogs ($m^7Gppp^{5'S}ApG$ and $m^7Gppp^{5'S}A_mpG$)

Dinucleotide 5'-phosphorothiolate $p^{5'S}NpG$, 7-methyl-guanosine-5'-diphosphate $P^2$-imidazolide $m^7GDP$-Im[15] (2 equivalents) and $ZnCl_2$ (20 equivalents) were dissolved in DMSO (to 0.05 M of $p^{5'S}NpG$) and the mixture was stirred at room temperature for 3 days. The reaction was quenched by addition of a solution of $Na_2EDTA$ (20 mg/mL; 20 equivalents) and $NaHCO_3$ (10 mg/mL) in water and the product was isolated by ion-exchange chromatography on DEAE Sephadex (gradient elution 0-1.2 M TEAB) to afford after evaporation triethylammonium salt of $m^7Gppp^{5'S}NpG$. Additional purification by RP HPLC (C18) using a linear gradient of acetonitrile in aqueous $CH_3COONH_4$ buffer pH 5.9 provided (after repeated freeze-drying from water) ammonium salts of $m^7Gppp^{5'S}NpG$.

| Compound | Synthesis scale [μmol] | Yield [a] [μmol] | RP HPLC [b] $R_t$ [min] | $m/z_{calcd.}$ | $m/z_{found}$ |
|---|---|---|---|---|---|
| $m^7Gppp^{5'S}ApG$ | 15.9 | 1.22 | 6.393 | 1146.10981 | 1146.11080 |
| $m^7Gppp^{5'S}A_mpG$ | 10.5 | 1.17 | 7.353 | 1160.12546 | 1160.12658 |

[a] after RP HPLC;
[b] Linear gradient elution: 0-50% MeOH in $CH_3COONH_4$ pH 5.9 in 15 min Example 8: Synthesis of α,β-Methylenebisphosphonate Trinucleotide Cap Analogs ($m^7GppCH_2pApG$, $m^7GppCH_2pA_mpG$ and $m^7GppCH_2p^{m6}ApG$)

Dinucleotide 5'-methylenebisphosphonate $pCH_2pNpG$, 7-methylguanosine-5'-monophosphate P-imidazolide $m^7GMP\text{-}Im$[15] (5 equivalents) and $ZnCl_2$ (20 equivalents) were dissolved in DMSO (to 0.05 M of $pCH_2pNpG$) and the mixture was stirred at room temperature for 24 h. The reaction was quenched by addition of a solution of $Na_2EDTA$ (20 mg/mL; 20 equivalents) and $NaHCO_3$ (10 mg/mL) in water and the product was isolated by ion-exchange chromatography on DEAE Sephadex (gradient elution 0-1.2 M TEAB) to afford after evaporation triethylammonium salt of $m^7GppCH_2pNpG$. Additional purification by RP HPLC (C18) using a linear gradient of acetonitrile in aqueous $CH_3COONH_4$ buffer pH 5.9 provided (after repeated freeze-drying from water) ammonium salts of $m^7GppCH_2pNpG$.

| Compound | Synthesis scale [μmol] | Yield [a] [μmol] | RP HPLC [b] $R_t$ [min] | $m/z_{calcd.}$ | $m/z_{found}$ |
|---|---|---|---|---|---|
| $m^7GppCH_2pApG$ | 4.35 | 1.26 | 8.395 | 1128.15339 | 1128.15467 |
| $m^7GppCH_2pA_mpG$ | 12.7 | 10.8 | 9.973 | 1142.16904 | 1142.17023 |
| $m^7GppCH_2p^{m6}ApG$ | 8.78 | 4.53 | 9.721 | 1142.16904 | 1142.17006 |

[a] after RP HPLC;
[b] Linear gradient elution: 0-50% MeOH in $CH_3COONH_4$ pH 5.9 in 30 min $m^7GppCH_2pApG$: RP-HPLC: $R_t$=8.395 min; $^1H$ NMR (500 MHz, $D_2O$, 25° C.): δ=9.14 (s, 1H, $H8_{m7G}$), 8.47 (s, 1H, $H8_A$), 8.18 (s, 1H, $H2_A$), 7.95 (s, 1H, $H8_G$), 5.96 (d, $^3J_{H,H}$=5.1 Hz, 1H, $H1'_A$), 5.92 (d, $^3J_{H,H}$=3.4 Hz, 1H, $H1'_{m7G}$), 5.81 (d, $^3J_{H,H}$=5.5 Hz, 1H, $H1'_G$), 4.85-4.76 (m, overlapped with HDO, 1H, $H3'_A$), 4.75 (m, 2H, $H2'_A$, $H2'_G$) 4.60 (m, 1H, $H2'_{m7G}$), 4.52-4.46 (m, 3H, $H3'_G$, $H3'_{m7G}$, $H4'_A$), 4.38-4.32 (m, 3H, $H4'_{m7G}$, $H4'_G$, $H5'_G$), 4.30-4.11 (m, 5H, $H5'_A$, $H5_A$, $H5''_G$, $H5'_{m7G}$, $H5_{m7G}$), 4.03 (s, 3H, $N^7$—$CH_3$), 2.41 (t, $^2J_{H,P}$=19.8 Hz, 2H, P—$CH_2$—P) ppm; $^{31}P$ NMR (202.5 MHz, $D_2O$, $H_3PO_4$, 25° C.): δ=17.8 (m, 1P, $P_\alpha$), 8.7 (m, 1P, $P_\beta$), 0.3 (s, 1P, $P_G$), −10.2 (d, $^2J_{P,P}$=26.8 Hz, 1P, $P_\gamma$) ppm; HRMS ESI(−): m/z 1128.15467 (calcd for $C_{32}H_{42}N_{15}O_{23}P_4$ $[M-H]^-$ 1128.15339);

$m^7GppCH_2p(m^6{}_A)pG$: RP-HPLC: $R_t$=9.721 min; $^1H$ NMR (500 MHz, $D_2O$, 25° C.): δ=9.09 (s, 1H, $H8_{m7G}$), 8.30 (s, 1H, $H8_A$), 8.06 (s, 1H, $H2_A$), 7.88 (s, 1H, $H8_G$), 5.91 (d, $^3J_{H,H}$=4.6 Hz, 1H, $H1'_A$), 5.88 (d, $^3J_{H,H}$=3.1 Hz, 1H, $H1'_{m7G}$), 5.78 (d, $^3J_{H,H}$=5.3 Hz, 1H, $H1'_G$), 4.78-4.70 (m, 2H, $H3'_A$, $H2'_A$), 4.65 (dd, $^3J_{H,H}$=5.3 Hz, $3J_{H,H}$=5.3 Hz, 1H, $H2'_G$), 4.55 (m, 1H, $H2'_{m7G}$), 4.50 (m, 1H, $H4'_A$), 4.47 (m, 1H, $H3'_G$), 4.44 (m, 1H, $H3'_{m7G}$), 4.38-4.15 (m, 8H, $H4'_{m7G}$, $H5'_{m7G}$, $H4'_G$, $H5'_G$, $H5'_A$, $H5''_{m7G}$, $H5''_A$, $H5''_G$), 3.99 (s, 3H, $N^7$—$CH_3$), 3.04 (s, 3H, $N^6$—$CH_3$) 2.41 (t, $^2J_{H,P}$=19.0 Hz, 2H, P—$CH_2$—P) ppm; $^{31}P$ NMR (202.5 MHz, D20, $H_3PO_4$, 25° C.): δ=17.8 (m, 1P, $P_\alpha$), 8.7 (m, 1P, $P_\beta$), 0.3 (s, 1P, $P_G$), −10.2 (d, $^2J_{P,P}$=24.5 Hz, 1P, $P_\gamma$) ppm; HRMS ESI(−): m/z 1142.17009 (calcd for $C_{33}H_{44}N_{15}O_{23}P_4$ $[M-H]^-$ 1142.16904);

Biological Properties of the Compounds According to the Invention

Figure 2:
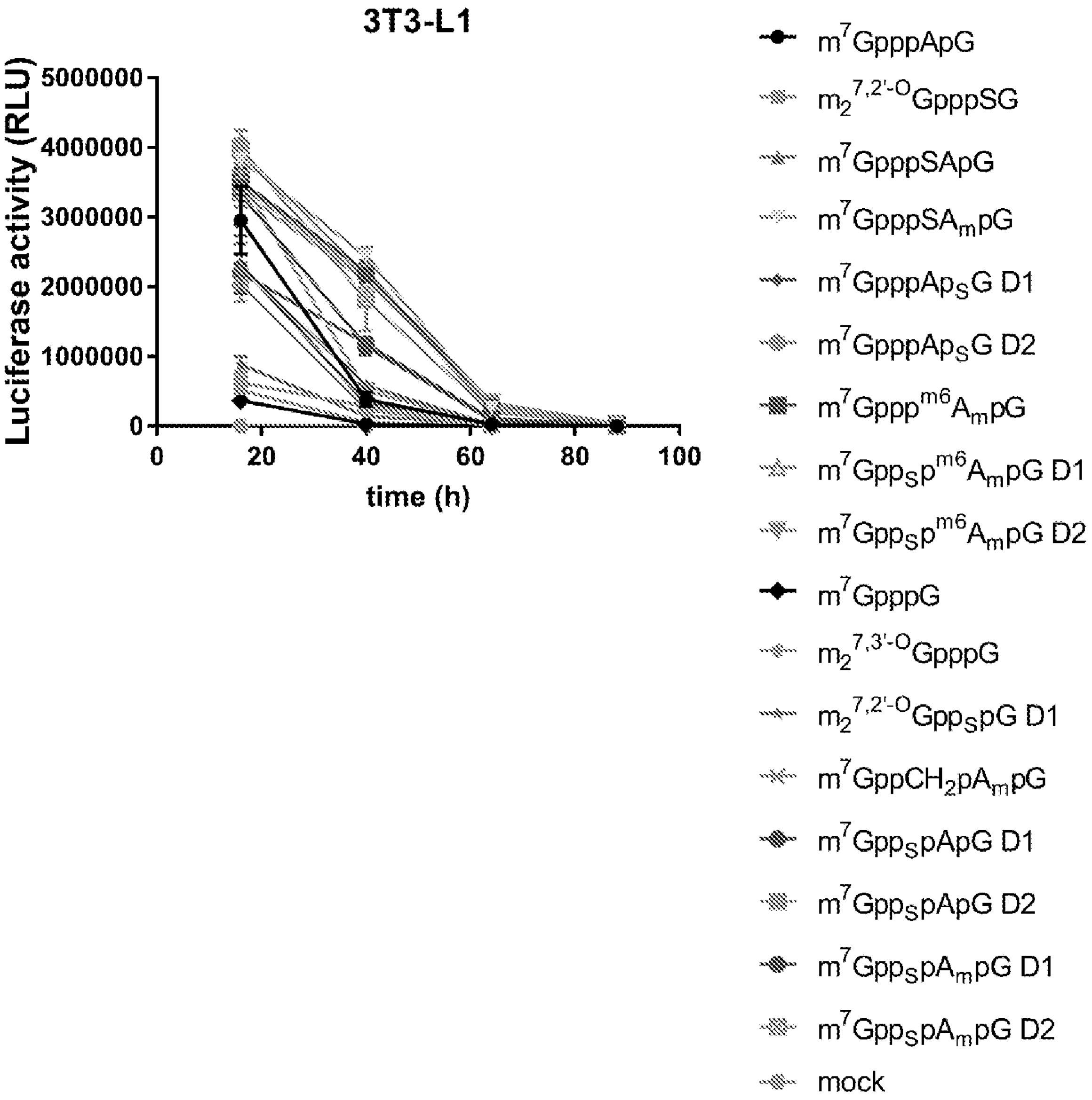
FIG. 2 shows protein expression in 3T3-L1 cells as a function of time obtained for enzymatically treated and HPLC-purified mRNA.
Figure 3:
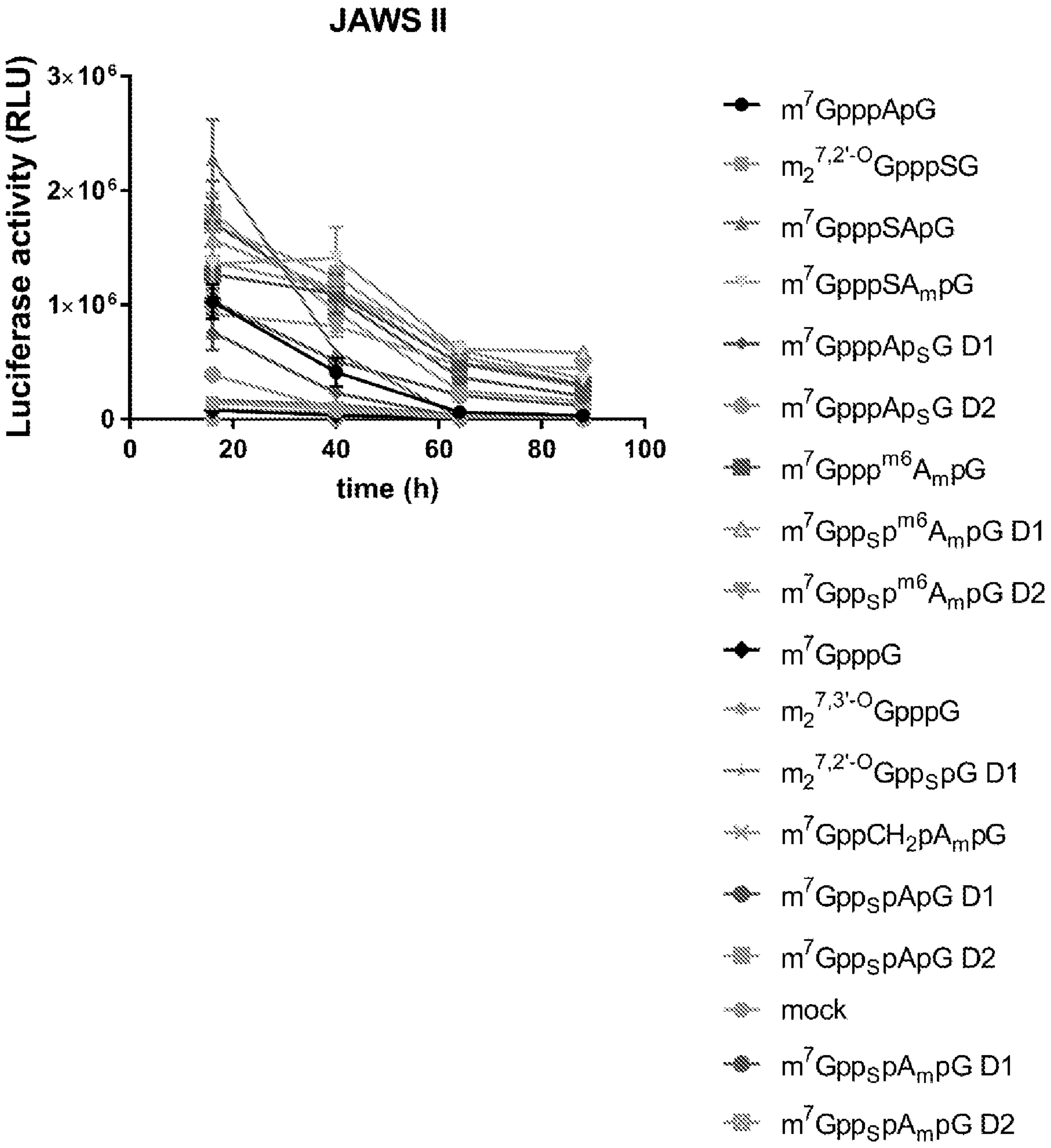
FIG. 3 shows protein expression in JAWSII cells as a function of time obtained for enzymatically treated and HPLC-purified mRNA.
Figure 4:
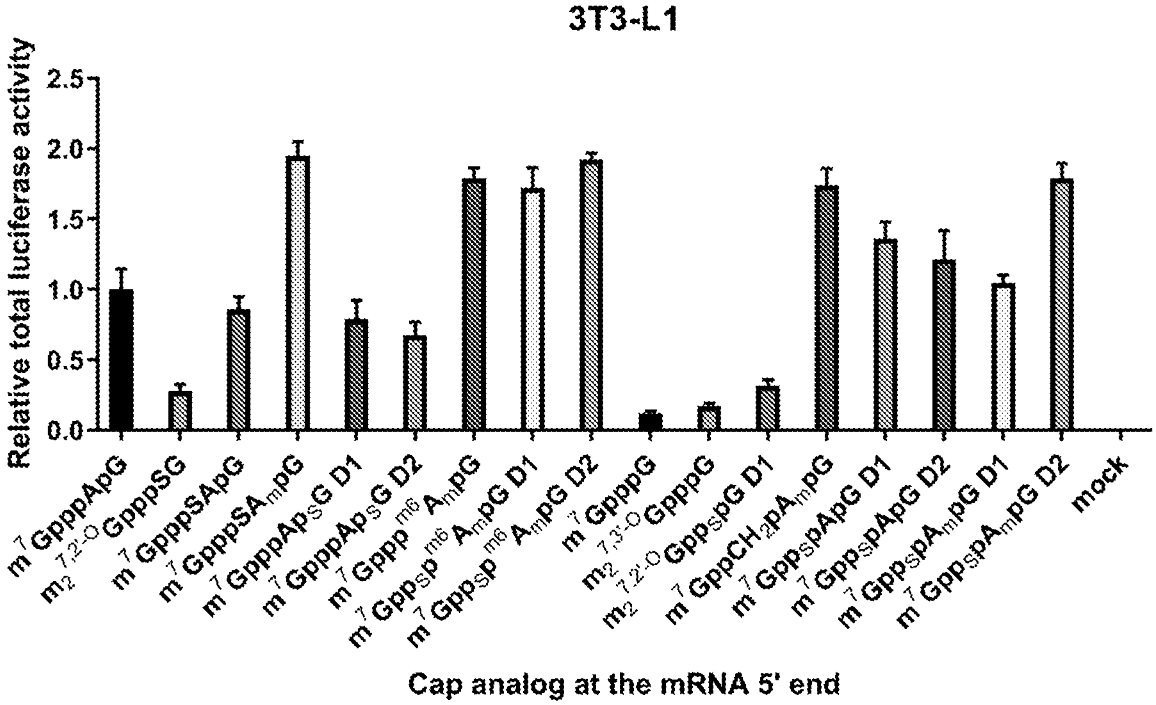
FIG. 4 shows the total protein expression in 3T3-L1 cells for enzymatically treated and HPLC-purified mRNA.
Figure 5:
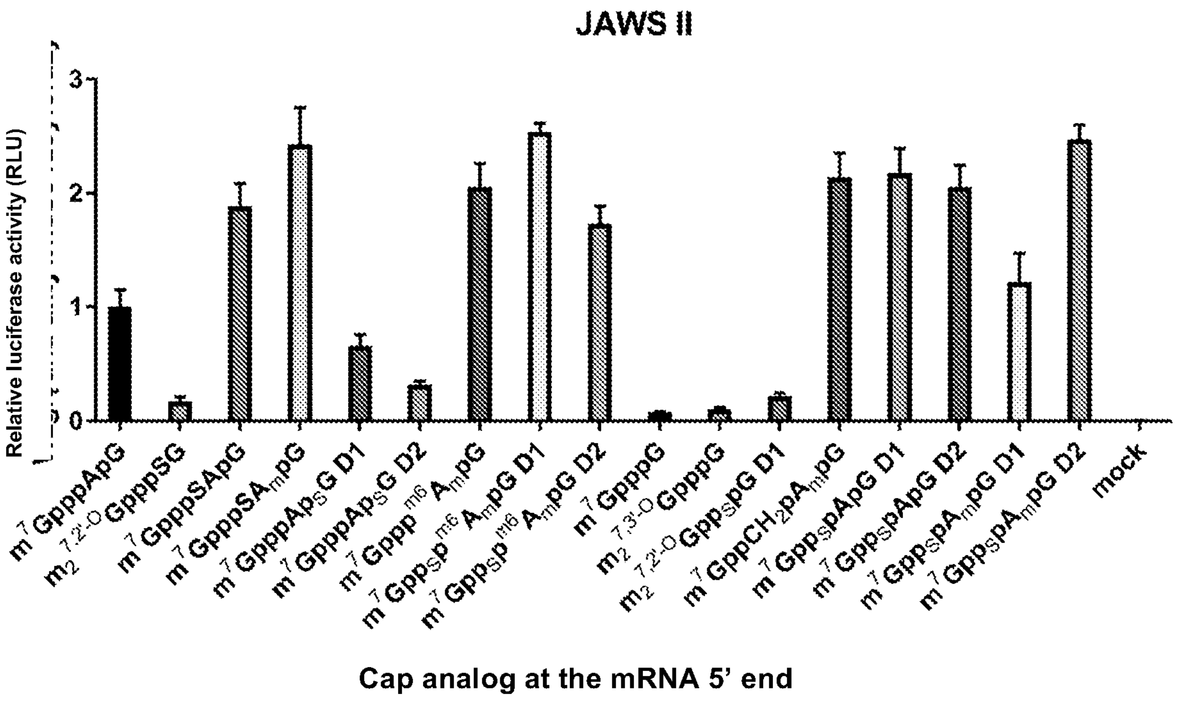
FIG. 5 shows the total protein expression in JAWSII cells for enzymatically treated and HPLC-purified mRNA.

Transcripts incorporating at the 5' end compounds according to the invention or benchmark (reference) compounds were obtained using in vitro transcription method in the presence of RNA polymerase T7 and DNA template containing the CD6.5 promoter sequence for this polymerase. In order to analyze the capping efficiency, short RNA transcripts were obtained as described in Example 9. The transcription yielding RNAs of 35 nt in length was carried out in the presence of selected compounds according to the invention or reference compounds representing state of the art and containing the same modifications of phosphate groups as the analyzed compounds according to the invention. The resulting RNAs were treated with DNAzyme 10-23 in order to shorten them and reduce 3' end heterogeneity and analyzed in 15% polyacrylamide gel, which enabled separation of capped and uncapped RNAs. The results of this analysis were shown in FIG. 1. In order to analyze protein expression yield in mammalian cells, mRNAs carrying compounds according to the invention or reference compounds and encoding Gaussia luciferase as a reporter gene were obtained. The in vitro transcription reaction was performed under conditions described in Example 10. The resulting mRNAs were subsequently subjected to a procedure of enzymatic removal of the uncapped (5'-triphosphate) RNA as described in Example 10, followed by RP HPLC purification to remove double stranded RNA impurities as described in Example 12. The obtained mRNAs were introduced into mammalian cell lines (fibroblasts—3T3-L1 and dendritic cells—JAWS II) using transfection with lipofectamine, followed by measuring Gaussia luciferase expression in the extracellular medium at appropriate time intervals by the luminescence method as described in Example 13. The results of these experiments as a function of time are shown in FIG. 2 and FIG. 3. Additionally, in FIG. 4 and FIG. 5 depicted are the overall (total) Gaussia luciferase expression levels achieved during the whole experiment duration (88 h), being the sum of Gaussia luciferase expression levels achieved at particular time-points.

Moreover, for selected compounds according to the invention, protein expression levels in JAWSII cells were also determined for in vitro transcribed mRNAs, which were not subjected to enzymatic removal of uncapped RNA impurities. The mRNAs used in these experiments were prepared as described in Example 11, whereas their purification by HPLC method and protein expression analysis were carried out as described in examples 12 and 13, respectively. The results of these experiments were depicted in FIG. 6 and FIG. 7.

Example 9: In Vitro Transcription of Short Capped RNAs and Capping Efficiency Analysis RNAs were generated on template of annealed oligonucleotides (CAGTAATACGACTCACTATAGGG-GAAGCGGGCATGCGGCCAGCCATAGCCGATCA and TGATCGGCTATGGCTGGCCGCATGCCCGCTTCCCC-TATAGTGAGTCGTATTACTG) [16], which contains T7 promoter sequence (TAATACGACTCACTATA) and encodes 35-nt long sequence (GGGGAAGCGGG-CATGCGGCCAGCCATAGCCGATCA). Typical in vitro transcription reaction (20 μl) was incubated at 37° C. for 2 h and contained: RNA Pol buffer (40 mM Tris-HCl pH 7.9, 10 mM $MgCl_2$, 1 mM DTT, 2 mM spermidine), 10 U/μl T7 RNA polymerase (ThermoFisher Scientific), 1 U/μl Ribo-Lock RNase Inhibitor (ThermoFisher Scientific), 2 mM ATP/CTP/UTP, 0.5 mM GTP, 2.5 mM cap analog of interests and 0.8 μM annealed oligonucleotides as a template. Following 2 h incubation, 1 U/μl DNase I (ThermoFisher Scientific) was added and incubation was continued for 30 min at 37° C. In order to generate homogenous 3'-ends in those RNAs, the transcripts (1 μM) were incubated with 1 μM DNAzyme 10-23 (TGATCGGCTAGGCTAGCTA-CAACGAGGCTGGCCGC) in 50 mM $MgCl_2$ and 50 mM Tris-HCl pH 8.0 for 1 h at 37° C. [16], which allowed to produce 3'-homogenous 25-nt RNAs. The transcripts were precipitated with ethanol and treated with DNase I in order to remove DNAzyme. Concentration of transcripts was determined spectrophotometrically. Capping efficiency of obtained RNAs was checked on 15% acrylamide/7 M urea gels.

Example 10: In Vitro Transcription of Capped mRNA with Subsequent Removal of RNAs Terminated with 5'-Triphosphate mRNAs encoding Gaussia luciferase were generated on template of pJET_T7_Gluc_128A plasmid digested with restriction enzyme AarI (ThermoFisher Scientifics). The plasmid was obtained by cloning the T7 promoter sequence and coding sequence of Gaussia luciferase into pJET_luc_128A.[12] aTypical in vitro transcription reaction (20 μl) was incubated at 37° C. for 2 h and contained: RNA Pol buffer (40 mM Tris-HCl pH 7.9, 10 mM $MgCl_2$, 1 mM DTT, 2 mM spermidine), 10 U/μl T7 RNA polymerase, 1 U/μl RiboLock RNase Inhibitor, 2 mM ATP/CTP/UTP, 0.5 mM GTP, 3 mM cap analog of interest and 50 ng/μl digested plasmid as a template. Following 2 h incubation, 1 U/μl DNase I was added and incubation was continued for 30 min at 37° C. The crude mRNAs were purified with NucleoSpin RNA Clean-up XS (Macherey-Nagel). Quality of transcripts was checked on native 1.2% 1×TBE agarose gel, whereas concentration was determined spectrophotometrically. To remove uncapped RNA, transcripts were treated with 5'-polyphosphatase (Epicentre) and Xrn1 (New England Biolabs). Briefly, mRNAs were incubated with 5'-polyphosphatase (20 U/5 μg of mRNA) in dedicated buffer for 30 min at 37° C., then mRNAs were purified with NucleoSpin RNA Clean-up XS. Purified mRNAs were subjected to incubation with Xrn-1 (1 U/1 μg of mRNA) in dedicated buffer for 60 min at 37° C., then mRNAs were purified with NucleoSpin RNA Clean-up XS.

Example 11: In Vitro Transcription of Capped mRNA without Subsequent Removal of RNAs Terminated with 5'-Triphosphate mRNAs encoding Gaussia luciferase were generated on template of pJET_T7_Gluc_$128_A$ plasmid digested with restriction enzyme AarI (ThermoFisher Scientifics). The plasmid was obtained by cloning the T7 promoter sequence and coding sequence of Gaussia luciferase into pJET_luc_128A.[12] Typical in vitro transcription reaction (20 μl) was incubated at 37° C. for 2 h and contained: RNA Pol buffer (40 mM Tris-HCl pH 7.9, 10 mM $MgCl_2$, 1 mM DTT, 2 mM spermidine), 10 U/μl T7 RNA polymerase, 1 U/μl RiboLock RNase Inhibitor, 2 mM ATP/CTP/UTP, 0.5 mM GTP, 3 mM cap analog of interest and 50 ng/μl digested plasmid as a template. Following 2 h incubation, 1 U/μl DNase I was added and incubation was continued for 30 min at 37° C. The crude mRNAs were purified with NucleoSpin RNA Clean-up XS (Macherey-Nagel). Quality of transcripts was checked on native 1.2% 1×TBE agarose gel, whereas concentration was determined spectrophotometrically.

Example 12: Purification of Capped mRNA Using HPLC mRNAs were purified on Agilent Technologies Series 1200 HPLC using RNASep™ Prep—RNA Purification Column (ADS Biotec) at 55° C. as described in [11]. For mRNA purification a linear gradient of buffer B (0.1 M triethylammonium acetate pH 7.0 and 25% acetonitrile) from 35% to 55% in buffer A (0.1 M triethylammonium acetate pH 7.0) over 22 min at 0.9 ml/min was applied. mRNAs was recovered from collected fractions by precipitation with isopropanol. Quality of transcripts was checked on native 1.2% 1×TBE agarose gel, whereas concentration was determined spectrophotometrically.

Example 13: Protein Expression Analysis

3T3-L1 (murine embryo fibroblast-like cells, ATCC CL-173) were grown in DMEM (Gibco) supplemented with 10% FBS (Sigma), GlutaMAX (Gibco) and 1% penicillin/streptomycin (Gibco) at 5% $CO_2$ and 37° C. Murine immature dendritic cell line JAWS II (ATCC CRL-11904) was grown in RPMI 1640 (Gibco) supplemented with 10% FBS, sodium pyruvate (Gibco), 1% penicillin/streptomycin and 5 ng/ml GM-CSF (PeproTech) at 5% $CO_2$ and 37° C. In a typical experiment, 104 of JAWS II cells and 4-103 of 3T3-L1 cells were seeded at the day of transfection in 100 μl medium without antibiotics per well of 96-well plate. Cells in each well were transfected for 16 h using a mixture of 0.3 μl Lipofectamine MessengerMAX Transfection Reagent (Invitrogen) and 25 ng mRNA in 10 μl Opti-MEM (Gibco). In order to assess Gaussia luciferase expression at multiple time points, medium was fully removed and replaced with the fresh one at each time point. To detect luminescence from Gaussia luciferase, 50 µl of 10 ng/ml h-coelenterazine (NanoLight) in PBS was added to 10 µl of cell cultured medium and the luminescence was measured on Synergy H1 (BioTek) microplate reader.

CONCLUSIONS

Examples 1-8 describe methods for obtaining trinucleotide cap analogs according to the inventon. The inventions covered by the claims, the synthesis of which has not been described in examples, can be obtained by methods identical or very similar to those exemplified.

Example 9 describes the method of performing capping efficiency analysis for RNAs obtained using the compounds accroding to the invention and comparing them with reference compounds representing state of the art. The results of the analysis indicate that in the case of trinucleotide cap analogs, used at fivefold excess over GTP, the capping efficiencies are significantly higher than in the case of dinucleotide cap analogs containing the same type of modifications and used at the same excess. As shown in FIG. 1 application of trinucleotide cap analogs enables increase of the incorporation efficiency into mRNA for triphosphate chain modifications of the cap. Moreover, the incorporation of triphosphate chain modifications using the trinucleotide cap analogs does not require the application of additional modifications of ARCA type (e.g. methylations of the 2'-O or 3'-O positions of 7-mehtylguanosine).

Figure 6:
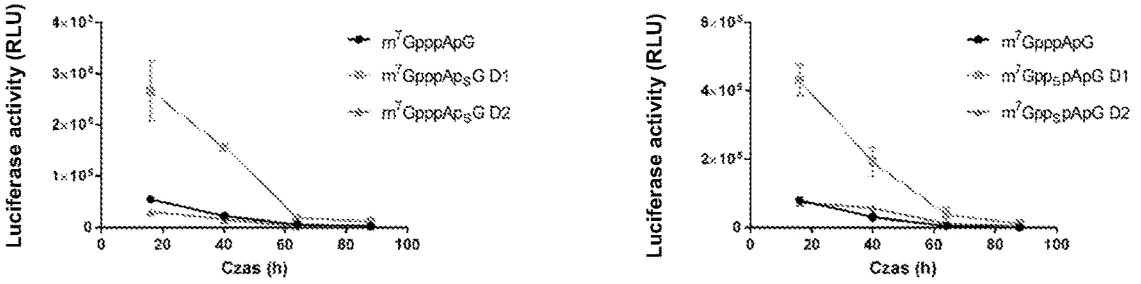
FIG. 6 shows protein expression in JAWSII cells as a function of time obtained for mRNAs that have not been subjected to the procedure of uncapped mRNA removal.
Figure 7:
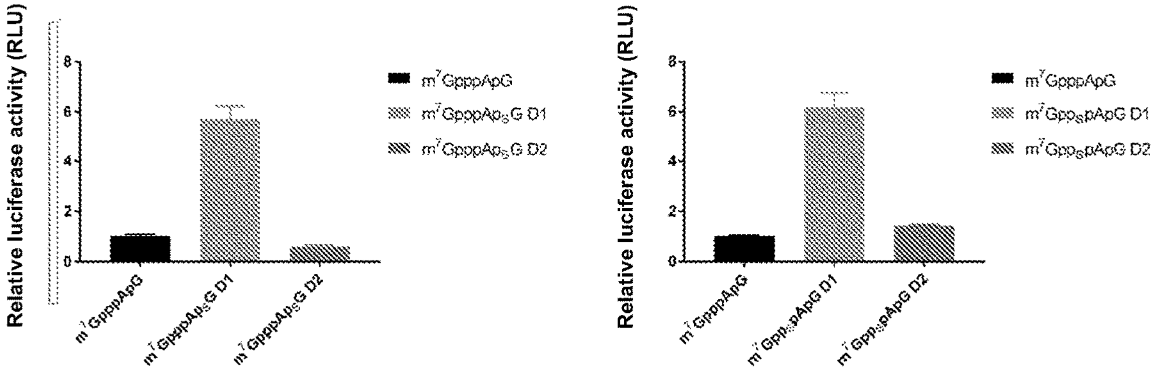
FIG. 7 shows the total protein expression in JAWSII cells for mRNAs that have not been subjected to the procedure of uncapped mRNA removal.

Examples 10, 11, 12 and 13 describe the approach to analyzing protein expression in mammalian cells from mRNAs according to the invention obtained with the use of compounds according to the invention. The analysis was performed in two cell lines representing cells of different origins (fibroblasts—3T3-L1 and dendritic cells—JAWS II) in two variants: (i) mRNA treated enzymatically to remove capped mRNA impurities (FIGS. 2, 3, 4 and 5) and (ii) enzymatically untreated mRNA (FIGS. 6 and 7). Each mRNA obtained with the use of compounds according to the invention showed higher protein expression compared to cap analogs representing the state of the art in at least one of the studied variants. Achieving augmented protein expression has found many applications in biotechnology and production of biopharmaceutics (production of recombinant proteins) as well as in mRNA based gene therapies. Increased protein expression in dendritic cells is particularly beneficial for applications in anti-cancer therapeutic vaccines. Augmented protein expression in cells derived from other tissues (lung, liver, other organs) is particularly beneficial in the case of gene replacement therapeutic applications.[18] It can be expected that achieving the therapeutic effect for mRNAs according to the invention obtained with the use of compounds according to the invention will be possible at lower mRNA concentrations then in the case of mRNAs obtained using state of the art methods. Lowering the mRNA dose implicates lower risk of side effects related to toxicity of the therapy, and thereby increases the probability of therapeutic success.

REFERENCES

1. Moore, M., From birth to death: The complex lives of eukaryotic mRNAs. *Science* 2005, 309 (5740), 1514-1518.
2. Ziemniak, M.; Strenkowska, M.; Kowalska, J.; Jemielity, J., Potential therapeutic applications of RNA cap analogs. *Future Medicinal Chemistry* 2013, 5 (10), 1141-1172.
3. Grudzien-Nogalska, E.; Stepinski, J.; Jemielity, J.; Zuberek, J.; Stolarski, R.; Rhoads, R. E.; Darzynkiewicz, E., Synthesis of anti-reverse cap analogs (ARCAs) and their applications in mRNA translation and stability. *Translation Initiation: Cell Biology, High-Throughput Methods, and Chemical-Based Approaches* 2007, 431, 203-227.
4. Sahin, U.; Kariko, K.; Tureci, O., mRNA-based therapeutics—developing a new class of drugs. *Nature Reviews Drug Discovery* 2014, 13 (10), 759-780.
5. Stepinski, J.; Waddell, C.; Stolarski, R.; Darzynkiewicz, E.; Rhoads, R. E., Synthesis and properties of mRNAs containing the novel "anti-reverse" cap analogs 7-methyl (3'-O-methyl)GpppG and 7-methyl(3'-deoxy)GpppG. *Rna—a Publication of the Rna Society* 2001, 7 (10), 1486-1495.
6. Jemielity, J.; Fowler, T.; Zuberek, J.; Stepinski, J.; Lewdorowicz, M.; Niedzwiecka, A.; Stolarski, R.; Darzynkiewicz, E.; Rhoads, R. E., Novel "anti-reverse" cap analogs with superior translational properties. *Rna—a Publication of the Rna Society* 2003, 9 (9), 1108-1122.
7. Jemielity, J.; Kowalska, J.; Rydzik, A. M.; Darzynkiewicz, E., Synthetic mRNA cap analogs with a modified triphosphate bridge—synthesis, applications and prospects. *New Journal of Chemistry* 2010, 34 (5), 829-844.
8. Grudzien-Nogalska, E.; Jemielity, J.; Kowalska, J.; Darzynkiewicz, E.; Rhoads, R. E., Phosphorothioate cap analogs stabilize mRNA and increase translational efficiency in mammalian cells. *Rna—a Publication of the Rna Society* 2007, 13 (10), 1745-1755.
9. Kuhn, A. N.; Diken, M.; Kreiter, S.; Selmi, A.; Kowalska, J.; Jemielity, J.; Darzynkiewicz, E.; Huber, C.; Tureci, O.; Sahin, U., Phosphorothioate cap analogs increase stability and translational efficiency of RNA vaccines in immature dendritic cells and induce superior immune responses in vivo. *Gene Therapy* 2010, 17 (8), 961-971.
10. Grudzien, E.; Kalek, M.; Jemielity, J.; Darzynkiewicz, E.; Rhoads, R. E., Differential inhibition of mRNA degradation pathways by novel cap analogs. *Journal of Biological Chemistry* 2006, 281 (4), 1857-1867.
11. Katalin Karikó, Hiromi Muramatsu, János Ludwig, Drew Weissman, Generating the optimal mRNA for therapy: HPLC purification eliminates immune activation and improves translation of nucleoside-modified, protein-encoding mRNA, Nucleic Acids Research, Vol. 39, Issue 21, 1 Nov. 2011, 142.
12. Sikorski, Pawel J; Warminski, Marcin; Kubacka, Dorota; Ratajczak, Tomasz; Nowis, Dominika; Kowalska, Joanna; Jemielity, Jacek; The identity and methylation status of the first transcribed nucleotide in eukaryotic mRNA 5' cap modulates protein expression in living cells. *Nucleic Acids Research* 2020, 305-1048.
13. M. Warminski et al. *Journal of the American Chemical Society* 2018, 140, 5987-5999.
14. M. Kalek, J. Jemielity, J. Stepinski, R. Stolarski, E. Darzynkiewicz, *Tetrahedron Letters* 2005, 46, 2417-2421.
15. J. Kowalska et al. *RNA* 2008, 14, 1119-1131.
16. Coleman, T., Wang, G. and Huang, F. (2004) Superior 5' homogeneity of RNA from ATP-initiated transcription under the T7 phi 2.5 promoter. *Nucleic Acids Research,* 32:e14

17. Norbert Pardi, Michael J. Hogan, Frederick W. Porter, Drew Weissman, N. Nature Reviews Drug Discovery vol. 17, 261-279 (2018).
18. Berraondo P, Martini P G V, Avila M A, et al Messenger *RNA* therapy for rare genetic metabolic diseases Gut 2019; 68:1323-1330.
19. Jin Wanga et. al., Nucleic Acids Research, Volume 47, Issue 20, 18 Nov. 2019,
20. Masahide Ishikawa, Ryuta Murai, Hiroyuki Hagiwara, Tetsuya Hoshino, Kamui Suyama, Nucleic Acids Symposium Series, Volume 53, Issue 1, September-October 2009, Pages 129-130.
21. Anand Ramanathan, G. Brett Robb, Siu-Hong Chan, Nucleic Acids Research, Volume 44, Issue 16, 19 Sep. 2016, Pages 7511-7526,
22. Pawel J Sikorski, Marcin Warminski, Dorota Kubacka, Tomasz Ratajczak, Dominika Nowis, Joanna Kowalska, Jacek Jemielity, Nucleic Acids Research, Volume 48, Issue 4, 28 Feb. 2020, Pages 1607-1626,
23. Sylwia Walczak et al., Chem. Sci., 2017, 8, 260-267.
24. U.S. Pat. No. 7,074,596B2
25. E. Grudzien Nogalska et al., Methods in Enzymology, Vol. 431, 2007, Pages 203-227.
26. Anna Maria Rydzik et. al., Organic & Biomolecular Chemistry, Issue 22, 2009.
27. M. Kalek et al., Bioorganic & Medicinal Chemistry, Vol. 14, Issue 9, 1 May 2006, Pages 3223-3230
28. J. Kowalska et. al. (2009), Phosphoroselenoate Dinucleotides for Modification of mRNA 5' End. ChemBioChem, 10: 2469-2473.
29. J. Kowalska, et. al., Nucleic Acids Research, Volume 42, Issue 16, 15 Sep. 2014, Pages 10245-10264,
30. A. Rydzik et. al., Nucleic Acids Research, Volume 45, Issue 15, 6 Sep. 2017, Pages 8661-8675,

The invention claimed is:
1. A compound selected from the group consisting of
(a) compound $m^7Gppp^{5'S}ApG$ of formula
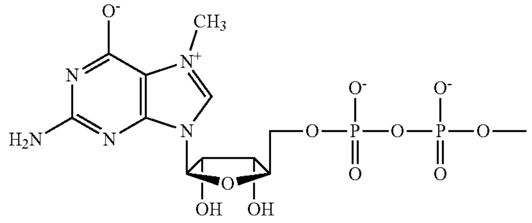
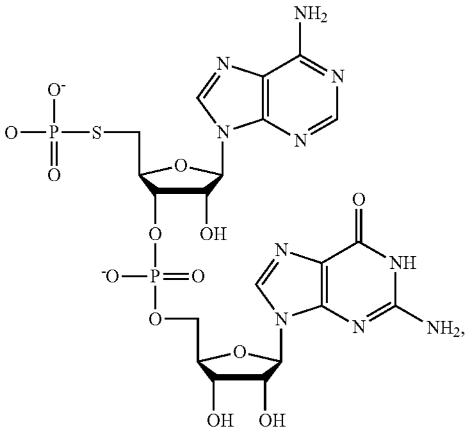
(b) compound $m^7Gppp^{5'S}A_mpG$ of formula
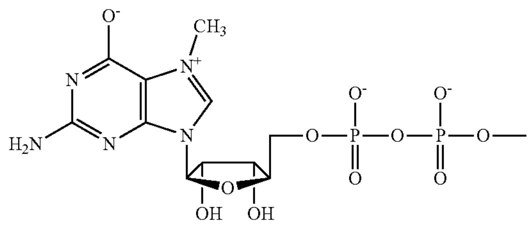
-continued
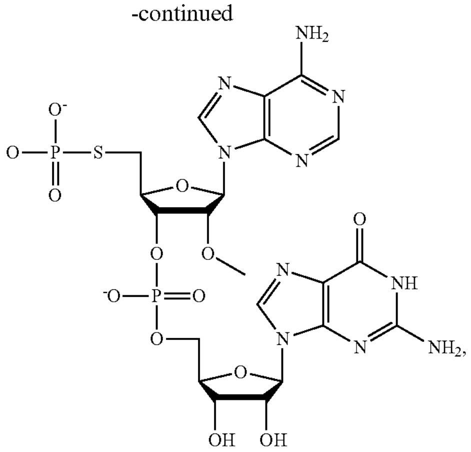
and
(c) a compound of formula (I)
(I)
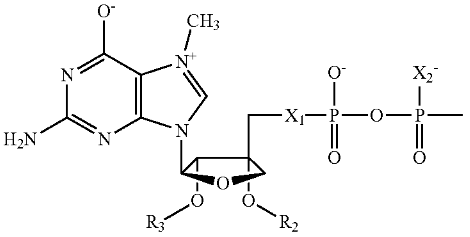
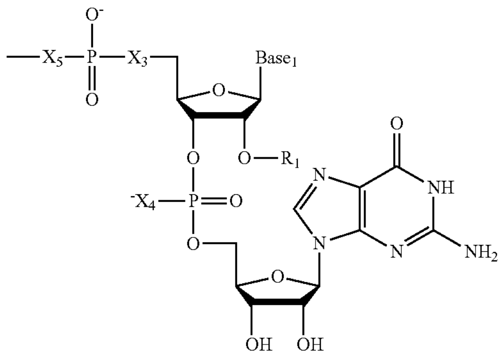

wherein:

$R_2$ is H, $R_3$ is H, $R_1$ is selected from the group consisting of: H, $CH_3$, alkyl, $Base_1$ is selected from the group consisting of:

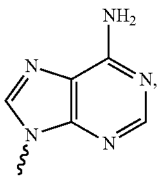

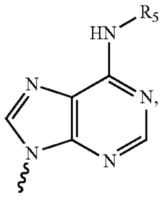

-continued

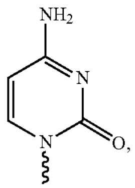

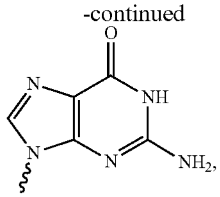

and

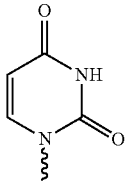

wherein $R_4$ is selected from the group consisting of: H, $CH_3$, alkyl, alkenyl, alkynyl, and alkylaryl, $X_1$ is O, $X_3$ is O or S, $X_2$ is O or S, $X_4$ is O or S, $X_5$ is O or $CH_2$, wherein $X_4$ is S, $X_5$ is $CH_2$, or both.

2. The compound according to claim 1, wherein said compound is selected from the group consisting of:

compound $m^7GpppAp_SG$ of formula:

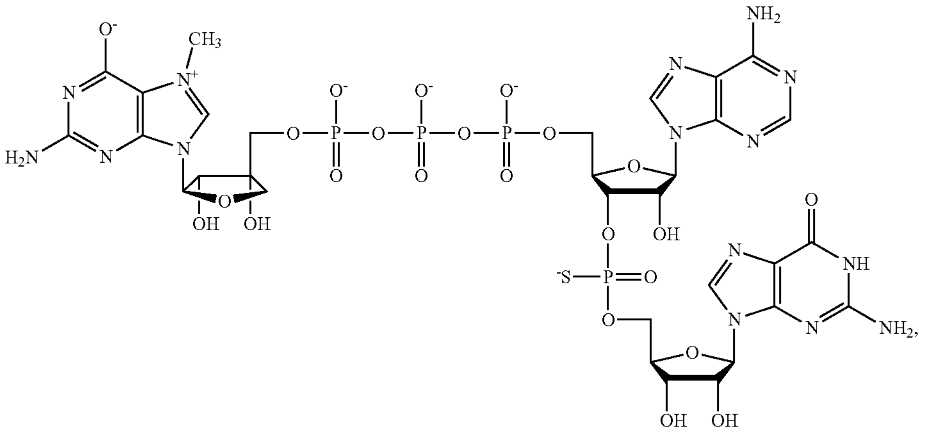

compound $m^7Gppp^{5'S}ApG$ of formula:

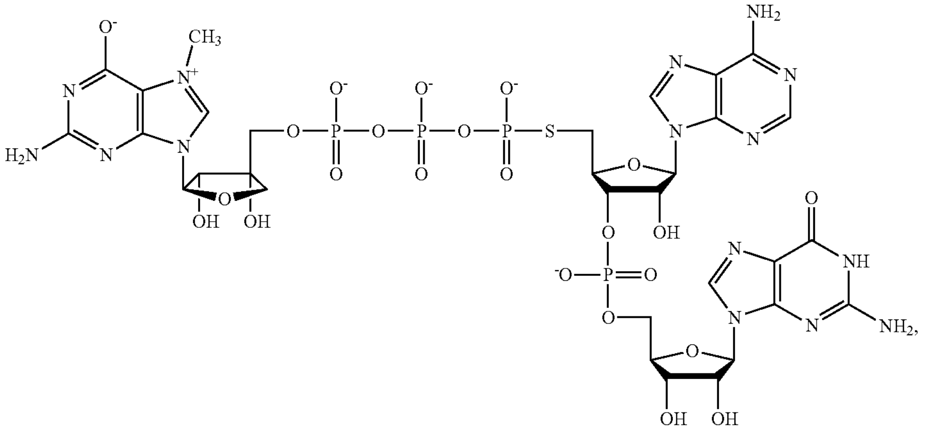

compound $m^7Gppp^{5'S}A_mpG$ of formula:
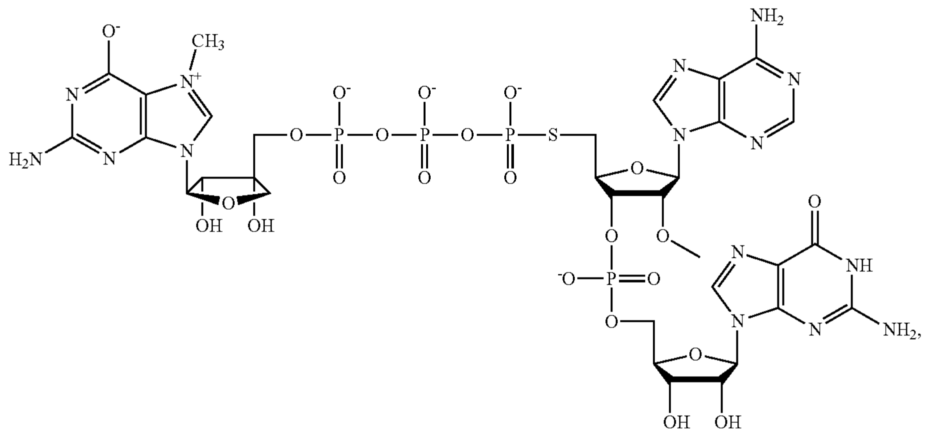
compound $m^7GppCH_2pApG$ with the formula:
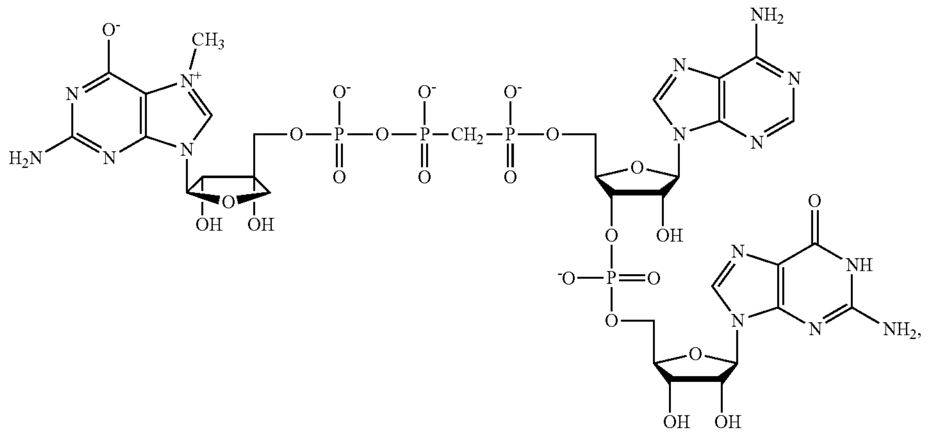
compound $m^7GppCH_2pA_mpG$ with the formula:
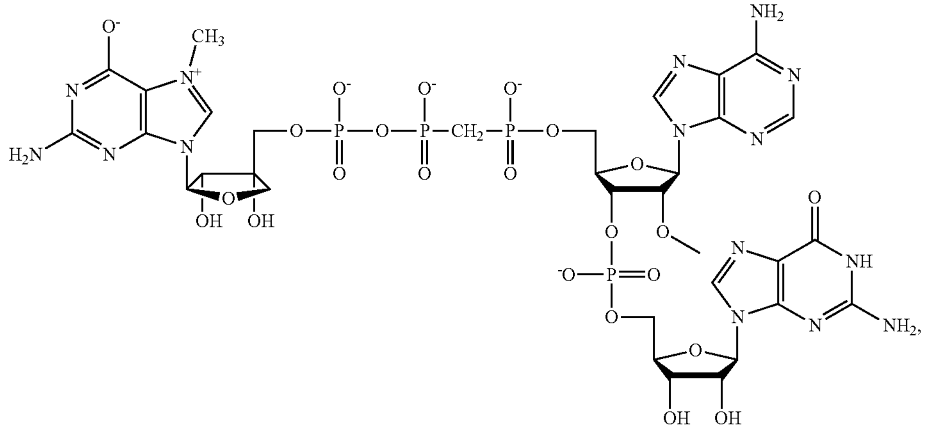

and compound $m^7GppCH_2p^{m6}ApG$ with the formula:

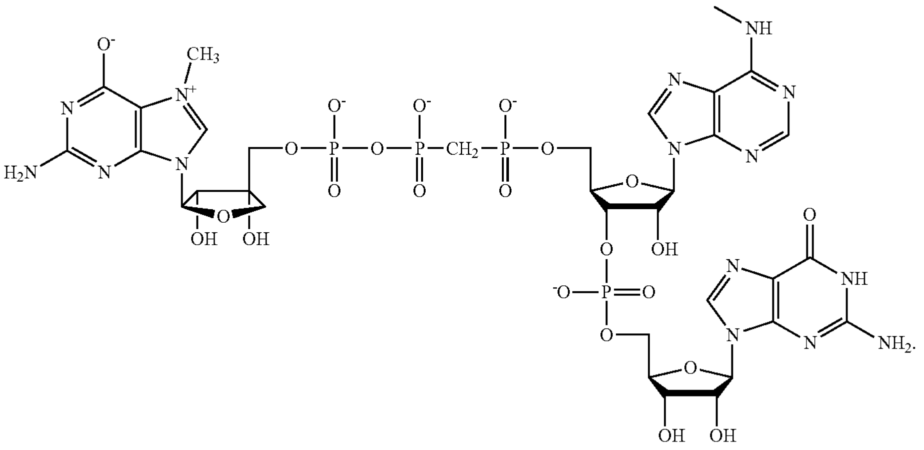

3. A compound according to claim 1, wherein said compound consists essentially of a single stereoisomer or comprises a mixture of at least two stereoisomers, a first diastereoisomer and a second diastereoisomer, the diastereoisomers being identical except that they have different stereochemical configurations around a stereogenic phosphorus atom, said stereogenic phosphorus atom being bonded to a sulfur atom, a selenium atom, or a borane group.

4. An RNA molecule which at the 5' end has a compound as defined in claim 1.

5. The compound according to claim 1, wherein the compound is selected from formula (I) and $X_4$ is S.

6. The compound according to claim 1, wherein the compound is selected from formula (I) and $X_5$ is $CH_2$.

7. The compound according to claim 1, wherein the compound is selected from formula (I), $X_4$ is S, and $X_5$ is $CH_2$.

8. The compound according to claim 1, wherein the compound is $m^7Gppp^{5'S}ApG$ of formula

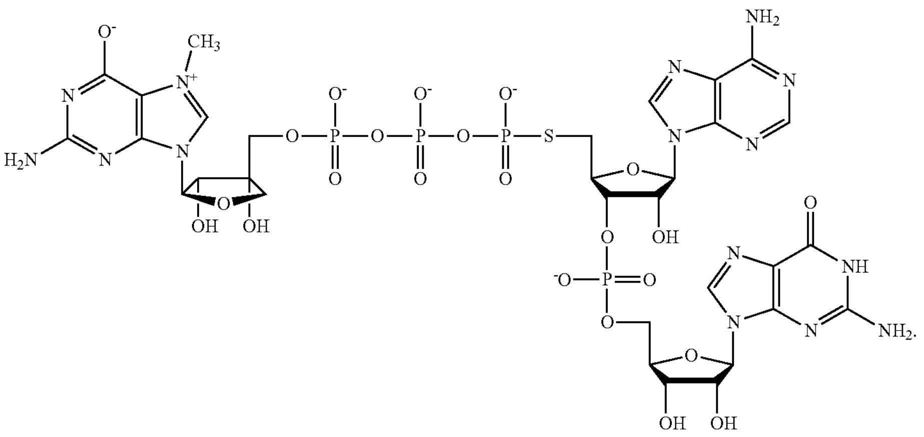

9. The compound according to claim 1, wherein the compound is $m^7Gppp^{5'S}A_mpG$ of formula
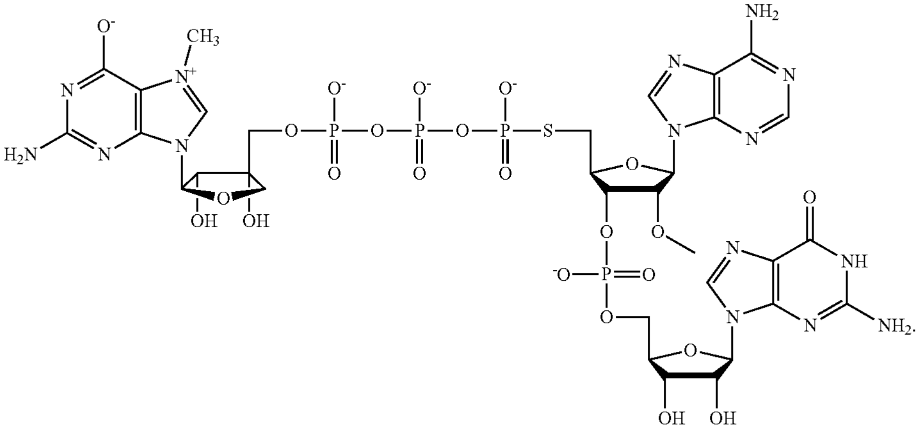
* * * * *

SEQUENCE LISTING

```
<160> NUMBER OF SEQ ID NOS: 5

<210> SEQ ID NO 1
<211> LENGTH: 55
<212> TYPE: DNA
<213> ORGANISM: artificial
<220> FEATURE:
<223> OTHER INFORMATION: oligonucleotide 1

<400> SEQUENCE: 1

cagtaatacg actcactata ggggaagcgg gcatgcggcc agccatagcc gatca          55


<210> SEQ ID NO 2
<211> LENGTH: 55
<212> TYPE: DNA
<213> ORGANISM: artificial
<220> FEATURE:
<223> OTHER INFORMATION: oligonucleotide 2

<400> SEQUENCE: 2

tgatcggcta tggctggccg catgcccgct tcccctatag tgagtcgtat tactg          55


<210> SEQ ID NO 3
<211> LENGTH: 17
<212> TYPE: DNA
<213> ORGANISM: T7

<400> SEQUENCE: 3

taatacgact cactata                                                    17


<210> SEQ ID NO 4
<211> LENGTH: 35
<212> TYPE: DNA
<213> ORGANISM: artificial
<220> FEATURE:
<223> OTHER INFORMATION: 35-nt long sequence

<400> SEQUENCE: 4

ggggaagcgg gcatgcggcc agccatagcc gatca                                35


<210> SEQ ID NO 5
<211> LENGTH: 35
<212> TYPE: DNA
<213> ORGANISM: artificial
<220> FEATURE:
<223> OTHER INFORMATION: DNAzyme 10-23
```

-continued
<400> SEQUENCE: 5
tgatcggcta ggctagctac aacgaggctg gccgc 35